(12) United States Patent
Maeta et al.

(10) Patent No.: US 11,267,904 B2
(45) Date of Patent: Mar. 8, 2022

(54) METHOD FOR CONTROLLING AFFINITY OF ANTIBODY FOR ANTIGEN, ANTIBODY WHOSE AFFINITY FOR ANTIGEN HAS BEEN ALTERED, AND ITS PRODUCTION METHOD

(71) Applicant: SYSMEX CORPORATION, Kobe (JP)

(72) Inventors: Shingo Maeta, Kobe (JP); Atsushi Fukunaga, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 452 days.

(21) Appl. No.: 15/855,508

(22) Filed: Dec. 27, 2017

(65) Prior Publication Data

US 2018/0179298 A1 Jun. 28, 2018

(30) Foreign Application Priority Data

Dec. 28, 2016 (JP) .............................. JP2016-255492
Aug. 10, 2017 (JP) .............................. JP2017-155840

(51) Int. Cl.
| | |
|---|---|
| *C07K 16/46* | (2006.01) |
| *C07K 16/28* | (2006.01) |
| *C07K 16/26* | (2006.01) |
| *C07K 16/40* | (2006.01) |
| *C07K 16/08* | (2006.01) |

(52) U.S. Cl.
CPC .......... *C07K 16/464* (2013.01); *C07K 16/082* (2013.01); *C07K 16/26* (2013.01); *C07K 16/28* (2013.01); *C07K 16/40* (2013.01); *C07K 2317/567* (2013.01); *C07K 2317/92* (2013.01); *C07K 2317/94* (2013.01)

(58) Field of Classification Search
None
See application file for complete search history.

(56) References Cited

U.S. PATENT DOCUMENTS

2012/0329995 A1 12/2012 Chang

FOREIGN PATENT DOCUMENTS

| WO | 2005/011376 A2 | 2/2005 |
| WO | 2013/084371 A1 | 6/2013 |

OTHER PUBLICATIONS

Quintero-Hernandez et al (MI, 44:1307-1315, 2007).*
Fukunaga A. et al. Improving the affinity of an antibody for its antigen via long-range electrostatic interactions, Protein Engineering, Design and Selection, Nov. 7, 2013, pp. 1-8, vol. 26, No. 12.
Lippow et al., "Computational design of antibody-affinity improvement beyond in vivo maturation", Nature Biotechnology, Oct. 2007, vol. 25, No. 10, XP-002615650, pp. 1171-1176 (total 6 pages).
Miller et al., "Stability engineering of scFvs for the development of bispecific and multivalent antibodies", Protection Engineering, design & Selection, 2010, vol. 23, No. 7, XP-002690428, pp. 549-557 (total 9 pages).
Fukunaga, A., "Study on improving the affinity of an antibody for its antigen via long-range electrostatic interactions", Kyushu university, 2013, pp. 1-48 (26 pages).
Novotny, J., et al., "Electrostatic Fields in Antibodies and Antibody/Antigen Complexes", Prog. Biophys. Molec. Biol., vol. 58, 1992, pp. 203-224 (22 pages).
Machine Translation of "Drug Delivery System," 2013, vol. 28-5, 18 pages.
The Japanese Office Action dated Aug. 20, 2019 in a counterpart Japanese patent application No. 2017-155840.
M. A. Holmes et al., "Structural Effects of Framework Mutations on a Humanized Anti-Lysozyme Antibody", The Journal of Immunology, American Association of Immunologists, US, vol. 167, No. 1, Jul. 1, 2001, pp. 296-301, XP002366459; Cited in the Communication pursuant to Article 94(3) EPC dated Apr. 30, 2020 in a counterpart European patent application.
The Communication pursuant to Article 94(3) EPC dated Apr. 30, 2020 in a counterpart European patent application No. 17210801.1.
Jefferson Foote et al: "Antibody Framework Residues Affecting the Conformation of the Hypervariable Loops", Journal of Molecular Biology, vol. 224, 1992, pp. 487-499.
The Japanese Office Action dated Nov. 10, 2020 in a counterpart Japanese patent application No. 2019-217139.
The Japanese Office Action dated Aug. 17, 2021 in a counterpart Japanese patent application No. 2019-217139.
Communication, dated Jan. 14, 2022, issued by the Japanese Patent Office in counterpart Japanese Application No. 2019-217139.

* cited by examiner

*Primary Examiner* — Brad Duffy
(74) *Attorney, Agent, or Firm* — Sughrue Mion, PLLC

(57) ABSTRACT

Disclosed is a method for controlling affinity of an antibody for an antigen, comprising substituting at least 3 amino acid residues of framework region 3 (FR3) defined by the Chothia method with charged amino acid residues, in an antibody whose electrical characteristic of complementarity determining region (CDR) based on the amino acid sequence of the CDR is neutral or negatively charged.

4 Claims, 4 Drawing Sheets

Specification includes a Sequence Listing.

ANTIGEN BINDING SITE

INSULIN
PI≈5.7

WILD TYPE
PI: 9.6

POSITIVELY
CHARGED
MUTATION
PI: 10.1

NEGATIVELY
CHARGED
MUTATION
PI: 7.9

ANTI-INSULIN ANTIBODY (Fab FRAGMENT)

ANTIGEN BINDING SITE

TSHR
PI≈5.9

WILD TYPE
PI: 9.8

POSITIVELY
CHARGED
MUTATION
PI: 10.2

NEGATIVELY
CHARGED
MUTATION
PI: 8.2

ANTI-TSHR ANTIBODY (Fab FRAGMENT)

METHOD FOR CONTROLLING AFFINITY OF ANTIBODY FOR ANTIGEN, ANTIBODY WHOSE AFFINITY FOR ANTIGEN HAS BEEN ALTERED, AND ITS PRODUCTION METHOD

CROSS REFERENCE TO RELATED APPLICATIONS

This application claims priority from prior Japanese Patent Application Nos. 2016-255492 filed on Dec. 28, 2016 and 2017-155840 filed on Aug. 10, 2017, entitled "Method for controlling affinity of antibody for antigen, antibody whose affinity for antigen has been altered, and its production method", the entire contents of which are hereby incorporated by reference.

TECHNICAL FIELD

The present invention relates to a method for controlling affinity of an antibody for an antigen. The present invention also relates to an antibody whose affinity for an antigen has been altered and its production method.

BACKGROUND

Conventionally, a technique for altering affinity of an antibody for an antigen by introducing a mutation into the amino acid sequence of the antibody has been known. For example, US 2012/0329995 A describes a method of introducing a mutation into the amino acid sequence of complementarity determining region (CDR) of an antibody to reduce the affinity of the antibody for an antigen.

It has been also known to alter affinity for an antigen by introducing a mutation into the amino acid sequence of the framework region in a variable region not into that of CDR. For example, Fukunaga A and Tsumoto K, Improving the affinity of an antibody for its antigen via long-range electrostatic interactions, Protein Eng. Des. Sel. Vol. 26, no. 12, p. 773-780, 2013 and WO 2013/084371 A describe that the 60th, 63rd, 65th and 67th amino acid residues located in the framework region 3 of the single chain antibody (scFv) binding to troponin I are substituted with a basic amino acid lysine or arginine residue. Troponin I is an antigen with a high content of charged amino acids. In Fukunaga A and Tsumoto K, Improving the affinity of an antibody for its antigen via long-range electrostatic interactions, Protein Eng. Des. Sel. Vol. 26, no. 12, p. 773-780, 2013 and WO 2013/084371 A, firstly, a single chain antibody recognizing an acidic epitope with a pI of 3.57 and a single chain antibody recognizing a basic epitope with a pI of 11.45 are prepared. Fukunaga A and Tsumoto K, Improving the affinity of an antibody for its antigen via long-range electrostatic interactions, Protein Eng. Des. Sel. Vol. 26, no. 12, p. 773-780, 2013 and WO 2013/084371 A describe that the affinity to troponin I could be improved by utilizing the electrical attraction generated by the introduction of basic amino acid residues into these single chain antibodies.

SUMMARY OF THE INVENTION

The scope of the present invention is defined solely by the appended claims, and is not affected to any degree by the statements within this summary.

In Fukunaga A and Tsumoto K, Improving the affinity of an antibody for its antigen via long-range electrostatic interactions, Protein Eng. Des. Sel. Vol. 26, no. 12, p. 773-780, 2013 and WO 2013/084371 A, from the viewpoint of increasing the binding rate constant in the antigen-antibody reaction, the mutation as described above is introduced in the framework region 3 (FR3) of the anti-troponin I antibody to improve the affinity for troponin I. However, these literatures do not describe whether antibodies other than anti-troponin I antibody can alter affinity for an antigen by the same method.

Also, Fukunaga A and Tsumoto K, Improving the affinity of an antibody for its antigen via long-range electrostatic interactions, Protein Eng. Des. Sel. Vol. 26, no. 12, p. 773-780, 2013 and WO 2013/084371 A describe only that the affinity for an antigen has been improved. On the other hand, when using an antibody as a reagent, not only an antibody with improved affinity for an antigen but also an antibody with reduced affinity may be required. For example, an antibody with reduced affinity for an antigen can be used as an appropriate control for antigen-antibody reactions. Therefore, establishment of a technique for controlling affinity of an antibody for an antigen is desired.

The present inventors have found that, by substituting the amino acid residue of FR3 of an antibody with a charged amino acid residue, the affinity for an antigen can be improved or reduced depending on the type of the antibody. Then, the present inventors have found that such difference in affinity change is related to the electrical characteristic of CDR determined based on the number of charged amino acid residues contained in the CDR, thereby completing the present invention.

Thus, a first aspect of the present invention provides a method for controlling affinity of an antibody for an antigen. In this method, in an antibody whose electrical characteristic of CDR based on the amino acid sequence of the CDR is neutral or negatively charged, at least 3 amino acid residues of FR3 defined by the Chothia method are substituted with charged amino acid residues.

Also, a second aspect of the present invention provides a method for producing an antibody whose affinity for an antigen has been altered. This method comprises the steps of substituting at least 3 amino acid residues of FR3 defined by the Chothia method with a charged amino acid residue in an antibody whose electrical characteristic of CDR based on the amino acid sequence of the CDR is neutral or negatively charged, and recovering the antibody obtained in the substitution step.

Furthermore, a third aspect of the present invention provides an antibody whose affinity for an antigen has been altered. In this antibody, the electrical characteristic of CDR based on the amino acid sequence of the CDR is neutral or negatively charged, and at least 3 amino acid residues of FR3 defined by the Chothia method in the unmodified antibody are substituted with charged amino acid residues.

DETAILED DESCRIPTION OF THE PREFERRED EMBODIMENTS

Figure 1A:
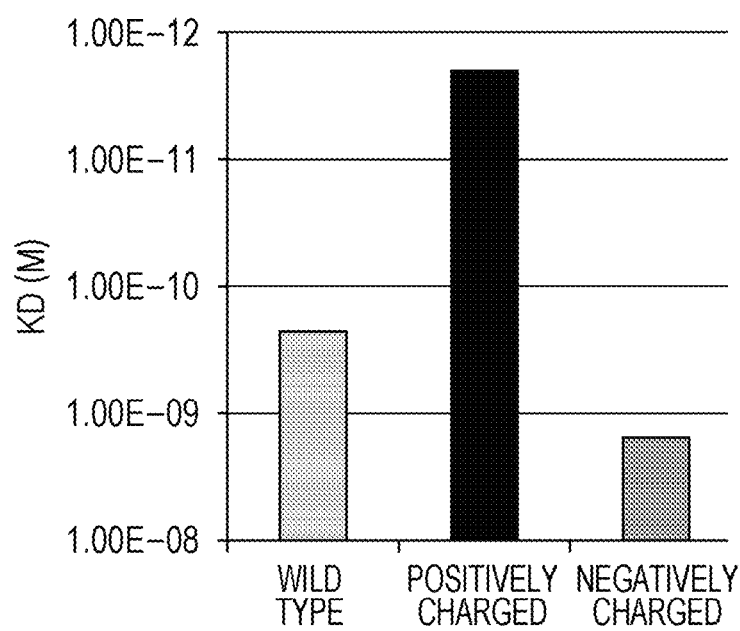
FIG. 1A is a graph showing a dissociation constant in an interaction between a wild-type anti-insulin antibody and its variant, and an antigen (insulin)

[1. Method for Controlling Affinity of Antibody for Antigen]

In the method for controlling affinity of an antibody for an antigen of the present embodiment (hereinafter, also referred to as "control method"), an antibody whose electrical characteristic of CDR based on the amino acid sequence of the CDR is neutral or negatively charged is for controlling the affinity for an antigen. In the control method of the present embodiment, in the antibody having such electrical characteristic, it is possible to control affinity of the antibody for an antigen by substituting at least 3 amino acid residues of FR3 defined by the Chothia method with charged amino acid residues. As used herein, the phrase "controlling affinity" refers to both improving the affinity of an antibody for an antigen and reducing the affinity of an antibody for an antigen. Therefore, the control method of the present embodiment may be interpreted as a method of altering affinity of an antibody for an antigen.

In the control method of the present embodiment, the original antibody for controlling the affinity for an antigen is also referred to as "unmodified antibody". Herein, substituting the amino acid residue of FR3 defined by the Chothia method in an unmodified antibody with a charged amino acid residue is also referred to as "introducing a mutation". Such substitution is also referred to as "introduction of mutation" or simply "mutation". An antibody obtained by introducing a mutation into an unmodified antibody is also referred to as "an antibody whose affinity is controlled".

In the present embodiment, the surface charge distribution of the unmodified antibody is changed by the introduction of mutation, and the affinity for an antigen is controlled. That is, the antibody whose affinity is controlled has improved or reduced affinity for an antigen as compared to the unmodified antibody. In the present embodiment, the affinity of the antibody whose affinity is controlled for an antigen may be evaluated by a kinetic parameter in an antigen-antibody reaction or may be evaluated by an immunological measurement method such as an ELISA method. The kinetic parameter includes binding rate constant ($k_{on}$), dissociation rate constant ($k_{off}$) and dissociation constant ($K_D$), and is preferably $K_D$. The kinetic parameter in an antigen-antibody reaction can be obtained by surface plasmon resonance (SPR) technology.

In the case where the affinity of the antibody for an antigen is improved by the control method of the present embodiment, for example, the value of $K_D$ in the antigen-antibody reaction is about ½, about ⅕, about 1/10, about 1/20, about 1/50, about 1/100 or about 1/1000, as compared to the unmodified antibody. On the other hand, when the affinity of the antibody for an antigen is reduced, the value of $K_D$ in the antigen-antibody reaction is about 2 times, about 5 times, about 10 times, about 20 times, about 50 times, about 100 times or about 1000 times, as compared to the unmodified antibody.

In the present embodiment, the unmodified antibody may be an antibody recognizing any antigen. In a preferred embodiment, the unmodified antibody is an antibody in which the base sequence of genes encoding the variable regions of light chain and heavy chain is known or an antibody in which the base sequence can be confirmed. Specifically, it is an antibody in which the base sequence of the antibody gene is disclosed in a known database, or an antibody in which the hybridoma producing the antibody is available. Examples of such database include GeneBank provided by National Center for Biotechnology Information (NCBI) and the like. The antibody class may be IgG, IgA, IgM, IgD or IgE, and is preferably IgG.

In the present embodiment, the unmodified antibody may be in the form of an antibody fragment as long as it has a variable region including FR3 to which a mutation is to be introduced. The antibody whose affinity is controlled may be in the form of an antibody fragment as long as it has a variable region including FR3 into which a mutation has been introduced. Examples of such antibody fragment include Fab fragments, F(ab')2 fragments, Fab' fragments, Fd fragments, Fv fragments, dAb fragments, single chain antibodies (scFv), and the like. Among them, Fab fragments are particularly preferred.

Three CDRs are present in each variable region of the light chain and heavy chain of the antibody and constitute the antigen-binding site of the antibody. The three CDRs are called CDR1, CDR2 and CDR3, counting from the amino terminus of the antibody chain. Since the CDR is involved in the specificity of the antibody, in the present embodiment, it is preferable that the antibody whose affinity is controlled does not have a mutation in the CDR. That is, the amino acid sequence of the CDR of the antibody whose affinity is controlled is preferably the same as the amino acid sequence of the CDR of the unmodified antibody.

The framework region (FR) is a region other than the CDRs present in each variable region of the light chain and heavy chain of the antibody. FR plays a role of a scaffold linking the three CDRs and contributes to the structural stability of the CDR. Therefore, the amino acid sequence of FR is highly conserved between antibodies of the same species. FR3 is one of FRs, and refers to the region between CDR2 and CDR3.

In the art, a method of numbering the amino acid residues of the CDR (hereinafter, also referred to as "numbering method") for defining the boundary and length of the CDR is known. As such numbering method, for example, the Chothia method (Chothia C. and Lesk A M., Canonical Structures for the Hypervariable Regions of Immunoglobulins., J Mol Biol., vol. 196, p. 901-917, 1987), the Kabat method (Kabat E A. et al., Sequences of Proteins of Immunological Interest., NIH publication No. 91-3242), the IMGT method (Lefranc M P., IMGT Unique Numbering for the Variable (V), Constant (C), and Groove (G) Domains of IG, TR, MH, IgSF, and MhSF., Cold Spring Harb Protoc. 2011(6): 633-642, 2011), the Honegger method (Honegger A. et al., Yet Another Numbering Scheme for Immunoglobulin Variable Domains: An Automatic Modeling and Analysis Tool., J Mol Biol., vol. 309, p. 657-670, 2001), the ABM method, the Contact method and the like are known. When numbers are assigned to the amino acid residues of the CDRs, the FR that is a region other than the CDRs is also numbered. In the present embodiment, the boundary and length of CDR and FR3 are defined by the Chothia method, but they can also be defined by other numbering methods.

In the Chothia method, light chain FR3 is defined as a region consisting of amino acid residues 53 to 90, and heavy chain FR3 is defined as a region consisting of amino acid residues 56 to 95. Here, for comparison, the numbers of the light chain FR3 and heavy chain FR3 (the positions of the amino acid residues at the start and end points of FR3) as defined by the Chothia method and other numbering methods are shown in Tables 1 and 2. The Vernier zone residue in the table is an amino acid residue contributing to the structural stability of the CDR among the amino acid residues contained in the FR. Tables 1 and 2 also show the positions of the Vernier zone residues in FR3, as defined by the numbering methods. Table 1 also shows the positions where mutation was introduced in FR3 of the light chain in Example 1, as defined by the numbering methods.

TABLE 1

| Numbering method | Light chain FR3 | Vernier zone residue | Position where mutation was introduced in light chain FR3 in Example 1 |
| --- | --- | --- | --- |
| Chothia | 53-90 | 64, 66, 68, 69, 71 | 63, 65, 67, 70, 72 |
| Kabat | 57-88 | 64, 66, 68, 69, 71 | 63, 65, 67, 70, 72 |
| IMGT | 66-104 | 78, 80, 84, 85, 87 | 77, 79, 83, 86, 88 |
| Honergger | 78-108 | 80, 82, 84, 87, 89 | 79, 81, 83, 88, 90 |
| ABM | 57-88 | 64, 66, 68, 69, 71 | 63, 65, 67, 70, 72 |
| Contact | 56-88 | 64, 66, 68, 69, 71 | 63, 65, 67, 70, 72 |

TABLE 2

| Numbering method | Heavy chain FR3 | Vernier zone residue |
| --- | --- | --- |
| Chothia | 56-98 | 67, 69, 71, 73, 78, 93, 94 |
| Kabat | 66-94 | 67, 69, 71, 73, 78, 93, 94 |
| IMGT | 66-104 | 76, 78, 80, 82, 87 |
| Honergger | 78-108 | 78, 80, 82, 84, 89, 107, 108 |
| ABM | 59-94 | 67, 69, 71, 73, 78, 93, 94 |
| Contact | 59-92 | 67, 69, 71, 73, 78 |

In the present embodiment, at least three mutations may be introduced into any of the amino acid residues of FR3 defined by the Chothia method (hereinafter, also simply referred to as "FR3") in an unmodified antibody. Preferably, at least three mutations are introduced into amino acid residues in the region excluding amino acid residues that are folded into the interior of the molecule from FR3 and are not exposed to the surface (hereinafter, also referred to as "unexposed residues"). It is expected that, even when a mutation is introduced into an unexposed residue, it will not affect the surface charge, so it is preferable to exclude an unexposed residue from the position where a mutation is to be introduced. Specifically, the amino acid residues in the region excluding the unexposed residues from FR3 are the 53rd to 81st amino acid residues of the FR3 of the light chain, and the 56th to 88th amino acid residues of the FR3 of the heavy chain.

More preferably, at least three mutations are introduced into the amino acid residues in the region excluding the unexposed residues and the Vernier zone residues from FR3. As described above, it is because the Vernier zone residue contributes to the structural stability of the CDR. Specifically, the amino acid residues in the region excluding the unexposed residues and the Vernier zone residue from FR3 are the 53rd to 63rd, 65th, 67th, 70th and 72nd to 81st amino acid residues of the FR3 of the light chain, and the 56th to 66th, 68th, 70th, 72nd, 74th to 77th and 79th to 88th amino acid residues of the FR3 of the heavy chain.

Particularly more preferably, at least three mutations are introduced into amino acid residues whose side chains are oriented toward the molecular surface, among the amino acid residues in the region excluding the unexposed residues and the Vernier zone residues from FR3. The amino acid residues whose side chains are oriented toward the molecular surface are substituted with charged amino acid residues, whereby the contribution to the surface charge becomes larger. The amino acid residues whose side chains are oriented toward the molecular surface in FR3 refer to the 53rd, 54th, 56th, 57th, 60th, 63rd, 65th, 67th, 70th, 72nd, 74th, 76th, 77th and 79th to 81st amino acid residues of the FR3 of the light chain, and the 56th, 57th, 59th, 61st, 62nd, 64th to 66th, 68th, 70th, 72nd, 74th, 75th, 77th, 79th, 81st, 83rd, 84th and 86th to 88th amino acid residues of the FR3 of the heavy chain.

In the present embodiment, at least three mutations may be introduced in either the FR3 of the light chain or the FR3 of the heavy chain. From the viewpoint of thermal stability of the antibody, it is preferable to introduce at least three mutations in the FR3 of the light chain. When the FR3s of both the light chain and the heavy chain have a mutation, it is preferable to introduce at least three mutations in the FR3 of the light chain and introduce at least three mutations in the FR3 of the heavy chain.

In the present embodiment, the upper limit of the number of mutations introduced in FR3 is not particularly limited, but is preferably 16 amino acids or less. That is, the number of mutations in FR3 of the antibody whose affinity is controlled is specifically 3, 4, 5, 6, 7, 8, 9, 10, 11, 12, 13, 14, 15, or 16.

As described above, in the control method of the present embodiment, the surface charge distribution changes due to the introduction of mutation into the unmodified antibody, and the affinity for an antigen changes. Thus, it is preferred that at least all three mutations are substitutions with charged amino acid residues having the same charge. That is, it is preferred that at least all three mutations are substitutions at acidic amino acid residues or substitutions at basic amino acid residues.

The charged amino acid residue refers to an aspartic acid residue, a glutamic acid residue, a lysine residue, an arginine residue, and a histidine residue. The acidic amino acid residue refers to an aspartic acid residue and a glutamic acid residue. The basic amino acid residue refers to a lysine residue, an arginine residue, and a histidine residue. In the present embodiment, as a basic amino acid residue to be introduced in FR3 as a mutation, a lysine residue and an arginine residue are preferable.

In the present embodiment, at least three mutations to be introduced into the unmodified antibody may be a mutation that substitutes the neutral amino acid residue of FR3 with a charged amino acid residue. The neutral amino acid residues refer to an alanine residue, an asparagine residue, an isoleucine residue, a glycine residue, a glutamine residue, a cysteine residue, a threonine residue, a serine residue, a tyrosine residue, a phenylalanine residue, a proline residue, a valine residue, a methionine residue, a leucine residue, and a tryptophan residue.

As described above, in the present embodiment, an antibody whose electrical characteristic of CDR based on the amino acid sequence of the CDR is neutral or negatively charged is for controlling the affinity for an antigen. Herein, the electrical characteristic of CDR is an index uniquely defined by the present inventors. The electrical characteristic of CDR is determined based on the number of charged amino acid residues in the amino acid sequence of the CDR. Specifically, the electrical characteristic of CDR is determined by the following formula (I).

$$X=[\text{Number of basic amino acid residues in amino acid sequence of CDR}]-[\text{Number of acidic amino acid residues in amino acid sequence of CDR}] \quad (I)$$

wherein when X is −1, 0 or 1, the electrical characteristic of CDR is neutral, when X is 2 or more, the electrical characteristic of CDR is positively charged, and when X is −2 or less, the electrical characteristic of CDR is negatively charged.

The electrical characteristic of CDR is preferably determined based on the amino acid sequences of the CDRs of both the light chain and the heavy chain. In this case, the amino acid sequence of the CDR in the formula (I) refers to all amino acid sequences of CDR1, CDR2 and CDR3 of the light chain and CDR1, CDR2 and CDR3 of the heavy chain. In the present embodiment, it is preferable to substitute at least 3 amino acid residues of the FR3 of the light chain with charged amino acid residues, in an antibody whose electrical characteristic determined based on the amino acid sequences of the CDRs of both the light chain and the heavy chain is neutral or negatively charged.

The electrical characteristic of CDR may be determined for each of the light chain CDR and the heavy chain CDR. That is, when determining the electrical characteristic of the light chain CDR, the amino acid sequence of the CDR in the formula (I) refers to all amino acid sequences of CDR1, CDR2 and CDR3 of the light chain. When determining the electrical characteristic of the heavy chain CDR, the amino acid sequence of the CDR in the formula (I) refers to all amino acid sequences of CDR1, CDR2 and CDR3 of the heavy chain. In the present embodiment, it is preferable to substitute at least 3 amino acid residues of the FR3 of the light chain with charged amino acid residues, in an antibody whose electrical characteristic of the light chain CDR is neutral or negatively charged.

The amino acid sequence of the CDR can be obtained from a public database that discloses the sequence of the antibody gene. Alternatively, when there is a hybridoma that produces an unmodified antibody, the amino acid sequence of the CDR can be obtained by obtaining a nucleic acid encoding a heavy chain and a light chain from the hybridoma by a known method, and sequencing the base sequence of the nucleic acid.

The electrical characteristic of CDR differs depending on the antibody. For example, as shown in Example 3 described below, the light chain CDR of a wild-type (i.e., unmodified) anti-insulin antibody has one basic amino acid residue (arginine), and no acidic amino acid residue exists. Thus, the electrical characteristic of CDR of the wild-type anti-insulin antibody is defined as neutral (X=1). The light chain CDR of a wild-type anti-TSHR antibody has five acidic amino acid residues (aspartic acid), and no basic amino acid residue exists. Thus, the electrical characteristic of CDR of the wild-type anti-TSHR antibody is defined as negatively charged (X=−5).

In an unmodified antibody whose electrical characteristic of CDR is neutral, by substituting at least 3 amino acid residues of FR3 with acidic amino acid residues, a wide range of surface charges including the antigen-binding site of the antibody becomes negative. In addition, in an unmodified antibody whose electrical characteristic of CDR is neutral, by substituting at least 3 amino acid residues of FR3 with basic amino acid residues, a wide range of surface charges including the antigen-binding site of the antibody becomes positive. By such a change in the surface charge, electrostatic interaction (attraction or repulsion) is generated when the antibody and the antigen bind. That is, in an unmodified antibody whose electrical characteristic of CDR is neutral, by substituting at least 3 amino acid residues of FR3 with acidic amino acid residues, the affinity of the antibody for an antigen can be reduced as compared to that of the unmodified antibody. In addition, in an unmodified antibody whose electrical characteristic of CDR is neutral, by substituting at least 3 amino acid residues of FR3 with basic amino acid residues, the affinity of the antibody for an antigen can be improved as compared to that of the unmodified antibody.

In an antibody whose electrical characteristic of CDR is negatively charged, by substituting at least 3 amino acid residues of FR3 with acidic amino acid residues, a wide range of surface charges including the antigen-binding site of the antibody becomes negative. By such a change in the surface charge, electrostatic interaction (repulsion) is generated when the antibody and the antigen bind. That is, in an unmodified antibody whose electrical characteristic of CDR is negatively charged, by substituting at least 3 amino acid residues of FR3 with acidic amino acid residues, the affinity of the antibody for an antigen can be reduced as compared to that of the unmodified antibody.

In the present embodiment, a mutation can be introduced in FR3 of the unmodified antibody by known methods such as DNA recombination technology and other molecular biological techniques. For example, when there is a hybridoma that produces an unmodified antibody, as shown in Example 1 described later, RNA extracted from the hybridoma is used to synthesize each of a polynucleotide encoding the light chain and a polynucleotide encoding the heavy chain, by a reverse transcription reaction and a RACE (Rapid Amplification of cDNA ends) method. These polynucleotides are amplified by PCR using primers for introducing a mutation into at least 3 amino acid residues of FR3 to obtain a polynucleotide encoding the light chain into which a mutation has been introduced in FR3 and a polynucleotide encoding the heavy chain into which a mutation has been introduced in FR3. The obtained polynucleotide is incorporated into an expression vector known in the art to obtain an expression vector containing a polynucleotide encoding an antibody whose affinity is controlled. Here, the polynucleotide encoding the light chain and the polynucleotide encoding the heavy chain may be incorporated into one expression vector or may be separately incorporated into two expression vectors. The type of the expression vector is not particularly limited, and it may be an expression vector for mammalian cells or an expression vector for *E. coli*. By transducing or transfecting the obtained expression vector into an appropriate host cell (for example, mammalian cell or *E. coli*), an antibody whose affinity is controlled can be obtained.

When obtaining an antibody whose affinity is controlled which is a single chain antibody (scFv), as shown in, for example, WO 2013/084371 A, RNA extracted from the hybridoma may be used to synthesize each of a polynucleotide encoding a light chain variable region and a polynucleotide encoding a heavy chain variable region by a reverse transcription reaction and PCR. These polynucleotides are ligated by overlap extension PCR or the like to obtain a polynucleotide encoding an unmodified scFv. The obtained polynucleotide is amplified by PCR using a primer for introducing a mutation into at least 3 amino acid residues of FR3 to obtain a polynucleotide encoding scFv into which a mutation has been introduced in FR3. The obtained polynucleotide is incorporated into an expression vector known in the art to obtain an expression vector containing a polynucleotide encoding an antibody whose affinity is controlled in the form of scFv. By transducing or transfecting the obtained expression vector into an appropriate host cell, an antibody whose affinity is controlled in the form of scFv can be obtained.

When there is no hybridoma that produces an antibody that recognizes an antigen of interest, an antibody-producing hybridoma may be prepared by known methods such as those described in, for example, Kohler and Milstein, Nature, vol. 256, p. 495-497, 1975. Alternatively, RNA obtained from the spleen of an animal such as a mouse immunized with an antigen of interest may be used. When the RNA obtained from the spleen is used, for example, as shown in Fukunaga A and Tsumoto K, Improving the affinity of an antibody for its antigen via long-range electrostatic interactions, Protein Eng. Des. Sel. Vol. 26, no. 12, p. 773-780, 2013, a polynucleotide encoding an unmodified Fab having desired affinity may be selected from among the polynucleotides encoding the obtained unmodified Fab by phage display method or the like.

[2. Method for Producing Antibody Whose Affinity for Antigen has been Altered]

The scope of the present disclosure also includes a method for producing an antibody (hereinafter, also referred to as "production method") whose affinity for an antigen has been altered. In the production method of the present embodiment, first, in an antibody whose electrical characteristic of CDR based on the amino acid sequence of the CDR is neutral or negatively charged, a step of substituting at least 3 amino acid residues of FR3 defined by the Chothia method with charged amino acid residues is carried out.

In the production method of the present embodiment, the antibody in which the amino acid residue of FR3 is substituted is the same as the unmodified antibody in the control method of the present embodiment. Hereinafter, in the production method of the present embodiment, the original antibody for altering affinity for an antigen is also referred to as "unmodified antibody". The details of the electrical characteristic of CDR are the same as those described for the control method of the present embodiment. The electrical characteristic of CDR of the antibody can be determined by the above formula (I). FR3 defined by the Chothia method is the same as that described for the control method of the present embodiment and is as shown in Tables 1 and 2.

In the production method of the present embodiment, it is possible to obtain an antibody whose affinity for an antigen has been altered by changing the surface charge distribution of the antibody by substitution of an amino acid residue. That is, it can be said that the above substitution step is, in the antibody whose electrical characteristic of CDR is neutral or negatively charged, a step of substituting at least 3 amino acid residues of FR3 defined by the Chothia method with charged amino acid residues to alter affinity of the antibody for an antigen. For example, the above substitution step may be, in an antibody whose electrical characteristic of CDR is neutral, a step of substituting at least 3 amino acid residues of FR3 defined by the Chothia method with acidic amino acid residues to reduce affinity of the antibody for an antigen as compared to that of the unmodified antibody. The above substitution step may be, in an antibody whose electrical characteristic of CDR is neutral, a step of substituting at least 3 amino acid residues of FR3 defined by the Chothia method with basic amino acid residues to improve affinity of the antibody for an antigen as compared to that of the unmodified antibody. Alternatively, the above substitution step may be, in an antibody whose electrical characteristic of CDR is negatively charged, a step of substituting at least 3 amino acid residues of FR3 defined by the Chothia method with acidic amino acid residues to reduce affinity of the antibody for an antigen as compared to that of the unmodified antibody.

In the present embodiment, it is preferable to substitute at least 3 amino acid residues of the FR3 of the light chain with charged amino acid residues, in an antibody whose electrical characteristic determined based on the amino acid sequences of the CDRs of both the light chain and the heavy chain is neutral or negatively charged. It is preferable to substitute at least 3 amino acid residues of the FR3 of the light chain with charged amino acid residues, in an antibody whose electrical characteristic of the light chain CDR is neutral or negatively charged.

Substitution of an amino acid residue can be carried out by known methods such as DNA recombination technology and other molecular biological techniques. For example, when there is a hybridoma that produces an antibody whose electrical characteristic of CDR is neutral or negatively charged, an expression vector containing a polynucleotide encoding an antibody whose affinity for an antigen has been altered is determined can be obtained in the same manner as described for the control method of the present embodiment. Moreover, by transducing or transfecting the obtained expression vector into an appropriate host cell, a host cell expressing the antibody can be obtained.

Then, in the production method of the present embodiment, the antibody obtained in the above substitution step is recovered. For example, a host cell expressing an antibody whose affinity for an antigen has been altered is dissolved in a solution containing an appropriate solubilizer to liberate the antibody in the solution. When the above host cell secretes an antibody whose affinity for an antigen has been altered into the medium, the culture supernatant is recovered. The liberated antibody can be recovered by methods known in the art such as affinity chromatography. For example, when the produced antibody is IgG, the antibody can be recovered by affinity chromatography using protein A or G. If necessary, the recovered antibody may be purified by methods known in the art such as gel filtration.

The affinity of the prepared antibody for an antigen may be evaluated by a kinetic parameter in an antigen-antibody reaction or may be evaluated by an immunological measurement method such as an ELISA method. In an antibody where the affinity for an antigen is improved, for example, the value of $K_D$ in the antigen-antibody reaction is about ½, about ⅕, about 1/10, about 1/20, about 1/50, about 1/100 or about 1/1000, as compared to the original antibody. In an antibody where the affinity for an antigen is reduced, the value of $K_D$ in the antigen-antibody reaction is about 2 times, about 5 times, about 10 times, about 20 times, about 50 times, about 100 times or about 1000 times, as compared to the original antibody.

[3. Antibody Whose Affinity for Antigen has been Altered]

The scope of the present disclosure also includes an antibody whose affinity for an antigen has been altered (hereinafter, also referred to as "modified antibody"). The modified antibody of the present embodiment is characterized in that the electrical characteristic of CDR based on the amino acid sequence of the CDR is neutral or negatively charged. The details of the electrical characteristic of CDR are the same as those described for the control method of the present embodiment. The electrical characteristic of CDR of the modified antibody can be determined by the above formula (I).

In the modified antibody of the present embodiment, at least 3 amino acid residues of FR3 defined by the Chothia method in an unmodified antibody are substituted with charged amino acid residues. That is, the modified antibody of the present embodiment has at least three mutations due to substitution with charged amino acid residues in FR3 defined by the Chothia method, as compared to the amino acid sequence of the unmodified antibody. The modified antibody of the present embodiment is the same as the above-described "antibody whose affinity is controlled". FR3 defined by the Chothia method is the same as that described for the control method of the present embodiment and is as shown in Tables 1 and 2.

Here, the unmodified antibody refers to an antibody before the affinity for an antigen is altered. That is, the unmodified antibody is the original antibody of the modified antibody, and the amino acid residue of FR3 defined by the Chothia method is not substituted with a charged amino acid residue. This unmodified antibody corresponds to the original antibody for controlling the affinity for an antigen in the control method of the present embodiment. In the present embodiment, the unmodified antibody has a CDR whose electrical characteristic is neutral or negatively charged.

In the modified antibody of the present embodiment, the surface charge distribution of the antibody is changed by the introduction of mutation. That is, the affinity of the modified antibody for an antigen is improved or reduced as compared to that of the unmodified antibody. In the present embodiment, the affinity of the modified antibody for an antigen may be evaluated by a kinetic parameter in an antigen-antibody reaction or may be evaluated by an immunological measurement method such as an ELISA method. The type and acquisition of the kinetic parameter are the same as those described for the control method of the present embodiment.

In a modified antibody where the affinity for an antigen is improved, for example, the value of $K_D$ in the antigen-antibody reaction is about ½, about ⅕, about 1/10, about 1/20, about 1/50, about 1/100 or about 1/1000, as compared to the unmodified antibody. In a modified antibody where the affinity for an antigen is reduced, for example, the value of $K_D$ in the antigen-antibody reaction is about 2 times, about 5 times, about 10 times, about 20 times, about 50 times, about 100 times or about 1000 times, as compared to the unmodified antibody.

The modified antibody may be an antibody recognizing any antigen. The antibody class may be IgG, IgA, IgM, IgD or IgE, and is preferably IgG. The modified antibody of the present embodiment may be in the form of an antibody fragment as long as it has a variable region including FR3 into which a mutation has been introduced. The type of the antibody fragment is the same as that described for the control method of the present embodiment.

It is preferable that the modified antibody of the present embodiment does not have a mutation in the CDR. That is, the amino acid sequence of the CDR of the modified antibody is preferably the same as the amino acid sequence of the CDR of the unmodified antibody.

In the modified antibody of the present embodiment, at least three mutations may be introduced into any amino acid residue of FR3 defined by the Chothia method in the unmodified antibody. Preferably, at least three mutations are introduced into the amino acid residues in the region excluding the unexposed residues from FR3. The amino acid residues in the region excluding the unexposed residues from FR3 are the same as those described for the control method of the present embodiment.

More preferably, at least three mutations are introduced into the amino acid residues in the region excluding the unexposed residues and the Vernier zone residues from FR3. The amino acid residues in the region excluding the unexposed residues and the Vernier zone residues from FR3 are the same as those described for the control method of the present embodiment.

Particularly more preferably, at least three mutations are introduced into amino acid residues whose side chains are oriented toward the molecular surface, among the amino acid residues in the region excluding the unexposed residues and the Vernier zone residues from FR3. The amino acid residues whose side chains are oriented toward the molecular surface in FR3 are the same as those described for the control method of the present embodiment.

In the present embodiment, mutations of at least 3 amino acid residues may be introduced into either the FR3 of the light chain or the FR3 of the heavy chain, but is preferably introduced into the FR3 of the light chain. When the FR3s of both the light chain and the heavy chain have a mutation, it is preferable to introduce mutations of at least 3 amino acid residues into the FR3 of the light chain and mutations of at least 3 amino acid residues into the FR3 of the heavy chain.

In the present embodiment, the upper limit of the number of mutations in FR3 of the modified antibody is not particularly limited, but is preferably 16 amino acids or less. Specifically, the number of mutations in FR3 of the modified antibody is 3, 4, 5, 6, 7, 8, 9, 10, 11, 12, 13, 14, 15 or 16.

In the present embodiment, at least three mutations of the modified antibody may be mutations in which the neutral amino acid residues of FR3 are substituted with charged amino acid residues. In the present embodiment, it is preferred that at least all three mutations are substitutions with charged amino acid residues having the same charge. That is, it is preferred that at least all three mutations are substitutions at acidic amino acid residues or substitutions at basic amino acid residues.

Examples of the modified antibody of the present embodiment include the following antibodies (1) to (3).

(1) An antibody whose electrical characteristic of CDR is neutral, at least 3 amino acid residues of FR3 defined by the Chothia method have been substituted with acidic amino acid residues, and the affinity of the antibody for an antigen is reduced as compared to that of an unmodified antibody, (2) An antibody whose electrical characteristic of CDR is neutral, at least 3 amino acid residues of FR3 defined by the Chothia method have been substituted with basic amino acid residues, and the affinity of the antibody for an antigen is improved as compared to that of an unmodified antibody, and (3) An antibody whose electrical characteristic of CDR is negatively charged, at least 3 amino acid residues of FR3 defined by the Chothia method have been substituted with acidic amino acid residues, and the affinity of the antibody for an antigen is reduced as compared to that of an unmodified antibody.

Specific examples of the modified antibody include modified antibodies of anti-insulin antibodies and anti-TSHR antibodies. In such a modified antibody of anti-insulin antibody, the electrical characteristic of CDR is neutral, and the 63rd, 65th, 67th, 70th and 72nd amino acid residues in the FR3 of the light chain are substituted with basic amino acid residues. In this modified antibody, the affinity for insulin, which is an antigen, is improved as compared to the unmodified antibody. On the other hand, in a modified antibody in which the 63rd, 65th, 67th, 70th and 72nd amino acid residues in the FR3 of the light chain have been substituted with acidic amino acid residues, the affinity for insulin, which is an antigen, is reduced as compared to the unmodified antibody. In the modified antibody of anti-TSHR antibody, the electrical characteristic of CDR is negatively charged, and the 63rd, 65th, 67th, 70th and 72nd amino acid residues in the FR3 of the light chain are substituted with acidic amino acid residues. In this modified antibody, the affinity for TSHR, which is an antigen, is reduced as compared to the unmodified antibody.

The modified antibody of the present embodiment can be prepared by known methods such as DNA recombination technology and other molecular biological techniques. For example, when there is a hybridoma that produces an antibody whose electrical characteristic of CDR is neutral or negatively charged, an antibody in which at least 3 amino acid residues of FR3 are substituted with charged amino acid residues can be prepared in the same manner as those described for the control method and the production method of the present embodiment.

In the present embodiment, the use method of the modified antibody is not particularly different from that of the unmodified antibody. The modified antibody can be used for various tests, research and the like, as well as the unmodified antibody. The modified antibody of the present embodiment may be modified with a labeling substance or the like known in the art.

The scope of the present disclosure also includes isolated and purified polynucleotides encoding an antibody whose affinity for an antigen has been altered of the present embodiment or fragments thereof. It is preferred that the isolated and purified polynucleotide encoding the fragment of the modified antibody of the present embodiment encodes a variable region including FR3 into which a mutation has been introduced. The scope of the present disclosure also includes a vector containing the above polynucleotide. A vector is a polynucleotide construct designed for transduction or transfection. The type of vector is not particularly limited. The vector can be appropriately selected from vectors known in the art such as expression vectors, cloning vectors, viral vectors and the like. The scope of the present disclosure also includes a host cell containing the vector. The type of the host cell is not particularly limited. The host cell can be appropriately selected from eukaryotic cells, prokaryotic cells, mammalian cells and the like.

Hereinafter, the present disclosure will be described in more detail by examples, but the present disclosure is not limited to these examples.

EXAMPLES

Example 1

Preparation of Antibody into which Charged Amino Acid Residue Introduced in FR3

Variants of each antibody were prepared by substituting 3 or 5 amino acid residues of FR3 of anti-insulin antibody and anti-thyroid-stimulating hormone receptor (TSHR) antibody with charged amino acid residues.

(1) Acquisition of Genes of Wild-Type Anti-Insulin Antibody and Wild-Type Anti-TSHR Antibody

[Reagents]

ISOGEN (NIPPON GENE CO., LTD.)

SMARTer (registered trademark) RACE 5'/3' kit (clontech)

10× A-attachment mix (TOYOBO CO., LTD.)

pcDNA (trademark) 3.4 TOPO (registered trademark) TA cloning kit (Thermo Fisher Scientific K.K.)

Competent high DH5α (TOYOBO CO., LTD.)

QIAprep Spin Miniprep kit (QIAGEN)

KOD plus neo (TOYOBO CO., LTD.)

Ligation high ver. 2 (TOYOBO CO., LTD.)

(1.1) Acquisition of Wild-Type Anti-Insulin Antibody Gene (1.1.1) Extraction of Total RNA from Antibody-Producing Hybridoma Hybridomas that produce a wild-type mouse anti-human insulin antibody were prepared by using human insulin as an antigen, according to the method described in Kohler and Milstein, Nature, vol. 256, p. 495-497, 1975. The hybridoma culture (10 mL) was centrifuged at 1000 rpm for 5 minutes, then the supernatant was removed. The resulting cells were dissolved with ISOGEN (1 mL). The solution was allowed to stand at room temperature for 5 minutes. Chloroform (200 μl) was added thereto, and the mixture was stirred for 15 seconds. Then, the mixture was allowed to stand at room temperature for 3 minutes. Then, this was centrifuged at 12000×G at 4° C. for 10 minutes, and an aqueous phase (500 μL) containing RNA was recovered. Isopropanol (500 μL) was added to the recovered aqueous phase, and the mixture was mixed. The resulting mixture was allowed to stand at room temperature for 5 minutes. Thereafter, the resulting mixture was centrifuged at 12000×G at 4° C. for 10 minutes. The supernatant was removed, and 70% ethanol (1 mL) was added to the resulting precipitate (total RNA). The mixture was centrifuged at 7500×G at 4° C. for 10 minutes. The supernatant was removed, and RNA was air-dried. The RNA was dissolved in RNase-free water (20 μL).

(1.1.2) Synthesis of cDNA

Using each of the total RNAs obtained in the above (1.1.1), RNA samples having the following composition were prepared.

[RNA Sample]

| | |
|---|---|
| Total RNA (500 ng/μL) | 1 μL |
| RT Primer | 1 μL |
| Deionized water | 1.75 μL |
| Total | 3.75 μL |

The prepared RNA sample was heated at 72° C. for 3 minutes. Thereafter, the RNA sample was incubated at 42° C. for 2 minutes. Then, a cDNA synthesis sample was prepared by adding 12 μM SMARTer II A oligonucleotide (1 μL) to the RNA sample. Using this cDNA synthesis sample, a reverse transcription reaction solution having the following composition was prepared.

[Reverse Transcription Reaction Solution]

| | |
|---|---|
| 5x First-Strand buffer | 2 μL |
| 20 mM DTT | 1 μL |
| 10 mM dNTP mix | 1 μL |
| RNase inhibitor | 0.25 μL |
| SMARTScribe RT(100 U/μL) | 1 μL |
| cDNA synthesis sample | 4.75 μL |
| Total | 10 μL |

The prepared reverse transcription reaction solution was reacted at 42° C. for 90 minutes. Then, the reaction solution was heated at 70° C. for 10 minutes, and tricine-EDTA (50 µL) was added thereto. Using the obtained solution as a cDNA sample, a 5'RACE reaction solution having the following composition was prepared.

[5'RACE Reaction Solution]

| | |
|---|---|
| 10x PCR buffer | 5 µL |
| dNTP mix | 5 µL |
| 25 mM Mg$_2$SO$_4$ | 3.5 µL |
| cDNA sample | 2.5 µL |
| 10x Universal Primer Mix | 5 µL |
| 3'-Primer | 1 µL |
| KOD plus neo (1 U/µL) | 1 µL |
| Purified water | 27 µL |
| Total | 50 µL |

The prepared 5'RACE reaction solution was subjected to RACE reaction under the following reaction conditions. The following "Y" is 90 seconds for the light chain and 150 seconds for the heavy chain.

[Reaction Conditions]

30 cycles at 94° C. for 2 minutes, 98° C. for 10 seconds, 50° C. for 30 seconds and 68° C. for Y seconds, and at 68° C. for 3 minutes.

Using the 5'RACE product obtained in the above reaction, a solution having the following composition was prepared. The solution was reacted at 60° C. for 30 minutes, and adenine was added to the end of the 5'RACE product.

| | |
|---|---|
| 5'RACE product | 9 µL |
| 10x A-attachment mix | 1 µL |
| Total | 10 µL |

A TA cloning reaction solution having the following composition was prepared using the resulting adenine addition product and pcDNA (trade name) 3.4 TOPO (registered trademark) TA cloning kit. The reaction solution was incubated at room temperature for 10 minutes, and the adenine adduct was cloned into pcDNA3.4.

[TA Cloning Reaction Solution]

| | |
|---|---|
| Adenine adduct | 4 µL |
| salt solution | 1 µL |
| pCDNA3.4 | 1 µL |
| Total | 6 µL |

(1.1.3) Transformation, Plasmid Extraction and Sequence Confirmation

The TA cloning sample (3 µL) obtained in the above (1.1.2) was added to DH5α (30 µL), and the mixture was allowed to stand on ice for 30 minutes. Thereafter, the mixture was heat shocked by heating at 42° C. for 45 seconds. The mixture was again allowed to stand on ice for 2 minutes, then the whole amount was applied to an ampicillin-containing LB plate. The plate was incubated at 37° C. for 16 hours. Single colonies on the plate were placed in the ampicillin-containing LB liquid medium, and the medium was shake-cultured (250 rpm) at 37° C. for 16 hours. The culture was centrifuged at 5000×G for 5 minutes to recover E. coli transformants. Plasmids were extracted from the recovered E. coli using the QIAprep Spin Miniprep kit.

Specific operations were carried out according to the manual attached to the kit. The base sequence of the obtained plasmid was confirmed using pcDNA3.4 vector primer. Hereinafter, this plasmid was used as a plasmid for expressing mammalian cells.

(1.2) Acquisition of Wild-Type Anti-TSHR Antibody Gene

Synthesis of wild-type human anti-TSHR antibody gene was entrusted to GenScript Japan Inc. to obtain the wild-type human anti-TSHR antibody gene.

(2) Acquisition of Genes of Variants of Each Antibody (2.1) Primer Design and PCR In order to introduce a mutation in FR3 defined by the Chothia method in the light chain of each antibody, PCR was carried out using the plasmid containing the wild-type anti-insulin antibody gene obtained in the above (1.1.3), the wild-type anti-TSHR antibody gene obtained in the above (1.2), and the primer represented by the following base sequence. A D5 variant is a variant in which 5 amino acid residues of FR3 are mutated to aspartic acid residues, a E5 variant is a variant in which 5 amino acid residues of FR3 are mutated to glutamic acid residues, a K5 variant is a variant in which 5 amino acid residues of FR3 are mutated to lysine residues, a R5 variant is a variant in which 5 amino acid residues of FR3 are mutated to arginine residues, and a R3 variant is a variant in which 3 amino acid residues of FR3 are mutated to arginine residues.

[Primer of Anti-Insulin Antibody]

```
Sequence 1 D5 Variant REV:
                                   (SEQ ID NO: 1)
5' TTCGTATTCGGTCCCTTCCCCTTCGCCTTCAAAGCGAGCA 3'

Sequence 2 E5 Variant REV:
                                   (SEQ ID NO: 2)
5' ATCGTAATCGGTCCCATCCCCATCGCCATCAAAGCGAGCA 3'

Sequence 3 K5 Variant REV:
                                   (SEQ ID NO: 3)
5' CTTGTACTTGGTCCCCTTCCCCTTGCCCTTAAAGCGAGCA 3'

Sequence 4 R5 Variant REV:
                                   (SEQ ID NO: 4)
5' TCTGTATCTGGTCCCTCTCCCTCTGCCTCTAAAGCGAGCA 3'

Sequence 5 FOR:
                                   (SEQ ID NO: 5)
5' CTCACAATCAGCTGATTG 3'

Sequence 6 R3 Variant REV:
                                   (SEQ ID NO: 6)
5' TCTCCCTCTGCCTCTAAAGCGAGCA 3'

Sequence 7 R3 Variant FOR:
                                   (SEQ ID NO: 7)
5' GGGACCAGATACAGA 3'
```

The primer of Sequence 5 was used as a forward primer common to the primers of Sequences 1 to 4. The primer of Sequence 7 was used as a forward primer for the primer of Sequence 6.

[Primer of Anti-TSHR Antibody]

```
Sequence 8 D5 Variant FOR:
                                   (SEQ ID NO: 8)
5' GGCACAGACGCCGACCTGGCAATCA 3'

Sequence 9 D5 Variant REV:
                                   (SEQ ID NO: 9)
5' GTCCCGGTCTCCGTCAAACCGGTCG 3'
```

-continued

```
Sequence 10 E5 Variant FOR:
                                (SEQ ID NO: 10)
5' GGCACAGAGGCCGAGCTGGCAATCA 3'

Sequence 11 E5 Variant REV:
                                (SEQ ID NO: 11)
5' CTCCCGCTCTCCCTCAAACCGGTCG 3'

Sequence 12 K5 Variant FOR:
                                (SEQ ID NO: 12)
5' GGCACAAAGGCCAAGCTGGCAATCA 3'

Sequence 13 K5 Variant REV:
                                (SEQ ID NO: 13)
5' CTTCCGCTTTCCCTTAAACCGGTCG 3'

Sequence 14 R5 Variant FOR:
                                (SEQ ID NO: 14)
5' GGCACAAGGGCCAGGCTGGCAATCA 3'

Sequence 15 R5 Variant REV:
                                (SEQ ID NO: 15)
5' CCTCCGCCTTCCCCTAAACCGGTCG 3'
```

Using the plasmid obtained in the above (1.3) as a template, a PCR reaction solution having the following composition was prepared.

[PCR Reaction Solution]

| | |
|---|---|
| 10x PCR buffer | 5 μL |
| 25 mM Mg$_2$SO$_4$ | 3 μL |
| 2 mM dNTP mix | 5 μL |
| Forward primer | 1 μL |
| Reverse primer | 1 μL |
| Template plasmid (40 ng/μL) | 0.5 μL |
| KOD plus neo (1 U/μL) | 1 μL |
| Purified water | 33.5 μL |
| Total | 50 μL |

The prepared PCR reaction solution was subjected to a PCR reaction under the following reaction conditions.

[Reaction Conditions]

30 cycles at 98° C. for 2 minutes, 98° C. for 10 seconds, 54° C. for 30 seconds and 68° C. for 4 minutes, and at 68° C. for 3 minutes.

The obtained PCR product was fragmented by adding 2 μL of DpnI (10 U/μL) to the PCR product (50 μL). Using the DpnI-treated PCR product, a ligation reaction solution having the following composition was prepared. The reaction solution was incubated at 16° C. for 1 hour to perform a ligation reaction.

[Ligation Reaction Liquid]

| | |
|---|---|
| DpnI-treated PCR product | 2 μL |
| Ligation high ver.2 | 5 μL |
| T4 Polynucleotide kinase | 1 μL |
| Purified water | 7 μL |
| Total | 15 μL |

(2.2) Transformation, Plasmid Extraction and Sequence Confirmation

A solution (3 μL) after the ligation reaction was added to DH5α (30 μL), and *E. coli* transformants were obtained in the same manner as in the above (1.1.3). Plasmids were extracted from the obtained *E. coli* using the QIAprep Spin Miniprep kit. The base sequence of each obtained plasmid was confirmed using pcDNA 3.4 vector primer. Hereinafter, these plasmids were used as plasmids for expressing mammalian cells.

(3) Expression in Mammalian Cells

[Reagents]
Expi293 (trademark) cells (Invitrogen)
Expi293 (trademark) Expression medium (Invitrogen)
ExpiFectamine (trademark) 293 transfection kit (Invitrogen)

(3.1) Transfection

Expi293 cells were proliferated by shaking culture (150 rpm) at 37° C. in a 5% CO$_2$ atmosphere. 30 mL of cell culture (3.0×10$^6$ cells/mL) was prepared according to the number of samples. A DNA solution of the following composition was prepared using a plasmid encoding each variant of FR3 and a plasmid encoding a wild-type antibody. The DNA solution was allowed to stand for 5 minutes.

[DNA Solution]

| | |
|---|---|
| Light chain plasmid solution | Amount (μL) corresponding to 15 μg |
| Heavy chain plasmid solution | Amount (μL) corresponding to 15 μg |
| Opti-MEM (trademark) | Appropriate amount (mL) |
| Total | 1.5 mL |

A transfection reagent having the following composition was prepared. The transfection reagent was allowed to stand for 5 minutes.

| | |
|---|---|
| ExpiFectamine reagent | 80 μL |
| Plasmid solution | 1420 μL |
| Total | 1.5 mL |

The prepared DNA solution and the transfection reagent were mixed. The mixture was allowed to stand for 20 minutes. The resulting mixture (3 mL) was added to the cell culture (30 mL). The mixture was shake-cultured (150 rpm) at 37° C. for 20 hours in a 5% CO$_2$ atmosphere. After 20 hours, 150 μL and 1.5 mL of ExpiFectamine (trademark) transfection enhancers 1 and 2 were added to each culture, respectively. Each mixture was shake-cultured (150 rpm) at 37° C. for 6 days in a 5% CO$_2$ atmosphere.

(3.2) Recovery and Purification of Antibody

Each cell culture was centrifuged at 3000 rpm for 5 minutes, and the culture supernatant was recovered. The culture supernatant contains each antibody secreted from transfected Expi293 (trademark) cells. The obtained culture supernatant was again centrifuged at 15000×G for 10 minutes, and the supernatant was recovered. To the resulting supernatant (30 mL) was added 100 μL of the antibody purification carrier Ab-Capcher Mag (ProteNova), and the mixture was reacted at room temperature for 2 hours. The carrier was magnetically collected to remove the supernatant, and PBS (1 mL) was added to wash the carrier. 400 μL of 100 mM Gly-HCl (pH 2.8) was added to the carrier, and the antibody (IgG) captured on the carrier was eluted. This elution operation was performed three times in total. The resulting eluate was neutralized with 100 mM Tris-HCl (pH 8.0) to obtain an antibody solution.

(4) Results

An antibody in which the 63rd, 65th, 67th, 70th and 72nd serine residues of the light chain FR3 defined by the Chothia method in the wild-type anti-insulin antibody and the wild-type anti-TSHR antibody were substituted with charged amino acid residues (aspartic acid residues, glutamic acid residues, lysine residues or arginine residues) was obtained. An antibody in which the 63rd, 65th and 67th serine residues of the light chain FR3 defined by the Chothia method in the wild-type anti-insulin antibody were substituted with charged amino acid residues (arginine residues) was obtained.

Example 2

Measurement of Affinity of Antibody into which Charged Amino Acid Residue Introduced in FR3

How the affinity of each variant prepared in Example 1 for an antigen changes as compared to that of the wild type was examined.

(1) Antibody Fragmentation

Using Pierce (trademark) Mouse IgG1 Fab and F(ab')2 Preparation kit (Thermo Fisher), each antibody obtained in Example 1 was made into Fab fragments. Specific operations were carried out according to the manual attached to the kit. The resulting reaction solution was subjected to gel filtration purification using Superdex 200 Increase 10/300 GL (GE Healthcare). The 50 kDa elution fraction was collected, and the obtained fraction was used as a Fab fragment-containing solution for subsequent experiments.

(2) Measurement of Affinity (2.1) Measurement of Affinity by SPR Technique

The affinity of wild-type anti-insulin antibody and its variant for an antigen was measured by SPR technique as follows. Humulin R U-100 (Eli Lilly) was used as an antigen for anti-insulin antibody. Antigen was immobilized (immobilization: 100 RU) to a sensor chip for Biacore (registered trademark) Series S Sensor Chip CM5 (GE Healthcare). 50 nM, 25 nM, 12.5 nM, 6.25 nM and 3.13 nM solutions were prepared by diluting the Fab fragment-containing solution of the anti-insulin antibody. Fab fragment-containing solutions at each concentration were delivered to Biacore (registered trademark) T200 (GE Healthcare) (association time of 120 seconds and dissociation time of 1200 seconds). Measurement data was analyzed using Biacore (registered trademark) Evaluation software, and the data on the affinity of anti-insulin antibody was obtained.

(2.2) Evaluation of Affinity by ELISA Method

The affinity of wild-type anti-TSHR antibody and its variant for an antigen was measured by ELISA method as follows.

(2.2.1) Immobilization of Capture Antibody

As a capture antibody, 4E31 antibody (RSR Limited), which was a mouse monoclonal anti-TSHR antibody, was used. The 4E31 antibody (5 µg) was diluted with PBS to obtain an antibody solution. 100 µL, each of this antibody solution was added to each well of NUNC-immuno module (Cat No. 469949, manufactured by NUNC, hereinafter referred to as "plate"). This plate was allowed to stand at room temperature for 3 hours to immobilize the 4E31 antibody on the well. The antibody solution was removed, and 300 µL each of a blocking solution (PBS containing 1% BSA) was added to each well of the plate. Blocking was performed at 4° C. for 20 hours or more.

(2.2.2) Primary Reaction

Detergent solubilized cell membrane preparation containing the TSHR (RSR Limited) was used as the antigen of the anti-TSHR antibody. This antigen was diluted 500-fold with PBS containing 1% BSA to obtain an antigen solution. The blocking solution was removed from the plate on which the 4E31 antibody was immobilized, and 50 µL each of the antigen solution was added to each well. This plate was shaken at room temperature for 60 minutes to perform an antigen-antibody reaction.

(2.2.3) Secondary Reaction

As detection antibodies, a wild-type anti-TSHR antibody, a D5 variant and a R5 variant were used. Each antibody was stepwise diluted with PBS containing 1% BSA to obtain antibody solutions at concentrations of 1000 pM, 100 pM, 10 pM, 1 pM, and 0.1 pM. HRP-labeled anti-human IgG (Fc specific) antibody was used as a secondary antibody. This secondary antibody was diluted with PBS containing 1% BSA to obtain a secondary antibody solution at a concentration of 0.2 µg/mL. The antibody solution (50 µL) of each concentration and the secondary antibody solution (50 µL) were mixed to obtain a mixed solution of antibodies. The antigen solution was removed from the plate, and 300 µL, each of a washing solution (PBS containing 1% BSA) was added to each well. Then, the washing solution was removed from the plate, and 300 µL each of washing solution was added to each well for washing. This washing operation was repeated three times. The washing solution was removed from the plate, and 100 µL each of the mixed solution of antibodies was added to each well. This plate was shaken at room temperature for 60 minutes to perform an antigen-antibody reaction. After the reaction, the above washing operation was repeated three times.

(2.2.4) Detection

As a substrate solution, 1-Step Ultra TMB-ELISA Substrate Solution (Thermo Fisher Scientific) was used. The washing solution was removed from the plate, and the substrate solution was added at 100 µL/well. This plate was allowed to stand at room temperature for 5 minutes. After 5 minutes, 100 µL each of a stop solution (0.1 M $H_2SO_4$) was added to each well of the plate to terminate the reaction. Then, the absorbance at 450 nm was measured for each well of the plate.

(3) Results

The dissociation constant ($K_D$) was calculated from the binding rate constant ($k_{on}$) and the dissociation rate constant ($k_{off}$) obtained for the anti-insulin antibody. The dissociation constant ($K_D$) was calculated from the measurement value of the ELISA method using the anti-TSHR antibody. The kinetic parameters of each antibody are shown in Tables 3 and 4, and FIGS. 1A and 1B. In the figures, "positively charged" indicates the $K_D$ value of the R5 variant, and "negatively charged" indicates the $K_D$ value of the D5 variant. In Table 3, the values obtained by global fitting are "average value±standard error".

TABLE 3

| Anti-insulin antibody | | | |
| --- | --- | --- | --- |
| Sample | $K_D$ (M) | $K_{on}$ ($M^{-1}s^{-1}$) | $K_{off}$ ($s^{-1}$) |
| Wild type | $2.22 \times 10^{-10}$ | $(2.48 \pm 0.01) \times 10^6$ | $(5.49 \pm 0.01) \times 10^{-4}$ |
| R3 Variant | $5.49 \times 10^{-11}$ | $(8.79 \pm 0.02) \times 10^6$ | $(4.83 \pm 0.01) \times 10^{-4}$ |
| R5 Variant | $2.03 \times 10^{-12}$ | $(7.19 \pm 0.05) \times 10^6$ | $(1.46 \pm 0.01) \times 10^{-5}$ |
| K5 Variant | $8.04 \times 10^{-12}$ | $(5.44 \pm 0.04) \times 10^7$ | $(4.37 \pm 0.01) \times 10^{-4}$ |
| D5 Variant | $9.69 \times 10^{-10}$ | $(7.64 \pm 0.04) \times 10^5$ | $(7.40 \pm 0.02) \times 10^{-4}$ |
| E5 Variant | $1.52 \times 10^{-9}$ | $(2.79 \pm 0.01) \times 10^5$ | $(4.24 \pm 0.01) \times 10^{-4}$ |

TABLE 4

| Anti-TSHR antibody | |
| --- | --- |
| Sample | $K_D$ (M) |
| Wild type | $7.0 \times 10^{-10}$ |
| D5 Variant | $3.0 \times 10^{-8}$ |
| R5 Variant | $6.5 \times 10^{-10}$ |

From Table 3 and FIG. 1A, the $K_D$ values of the R3 variant, the R5 variant and the K5 variant of the anti-insulin antibody were lower than the $K_D$ value of the wild type. The $K_D$ values of the D5 variant and the E5 variant were higher than the $K_D$ value of the wild type. Therefore, as to the anti-insulin antibody, it was found that an antibody with affinity for an antigen improved as compared to the wild type can be prepared by mutating 3 or 5 amino acid residues of FR3 to basic amino acid residues. It was found that an antibody with affinity for an antigen reduced as compared to the wild type can be prepared by mutating 5 amino acid residues of FR3 to acidic amino acid residues.

Figure 1B:
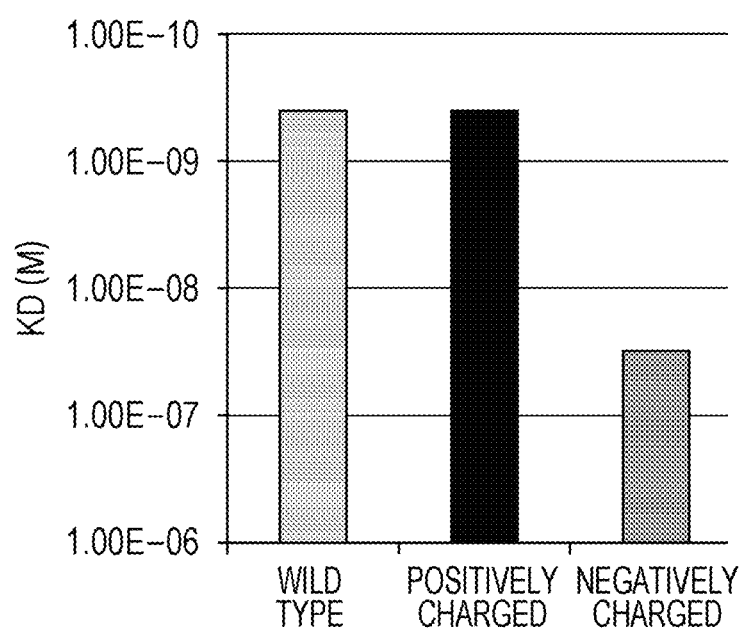
FIG. 1B is a graph showing a dissociation constant in an interaction between a wild-type anti-thyroid stimulating hormone receptor (TSHR) antibody and its variant, and an antigen (TSHR)

From Table 4 and FIG. 1B, the $K_D$ value of the D5 variant of the anti-TSHR antibody was higher than the $K_D$ value of the wild type. As to the anti-TSHR antibody, it was found that an antibody with affinity for an antigen reduced as compared to the wild type can be prepared by mutating 5 amino acid residues of FR3 to acidic amino acid residues. On the other hand, the $K_D$ value of the R5 variant of the anti-TSHR antibody was comparable to the $K_D$ value of the wild type. That is, as to the anti-TSHR antibody, it is suggested that affinity does not change even when 5 amino acid residues of FR3 are mutated to basic amino acid residues.

Example 3

Relationship Between Electrical Characteristic of Amino Acid Sequence of CDR and Affinity for Antigen From Example 2, as to the anti-insulin antibody, affinity could be improved and reduced by introducing mutation in FR3. On the other hand, as to the anti-TSHR antibody, affinity could be reduced even by introducing mutation in FR3, but affinity could not be improved. Therefore, the influence of the antigen-binding site of the antibody on the surface charge by introducing mutation in FR3 was examined.

(1) Study of Change in Antibody Surface Charge by Mutation Introduction

Figure 2A:
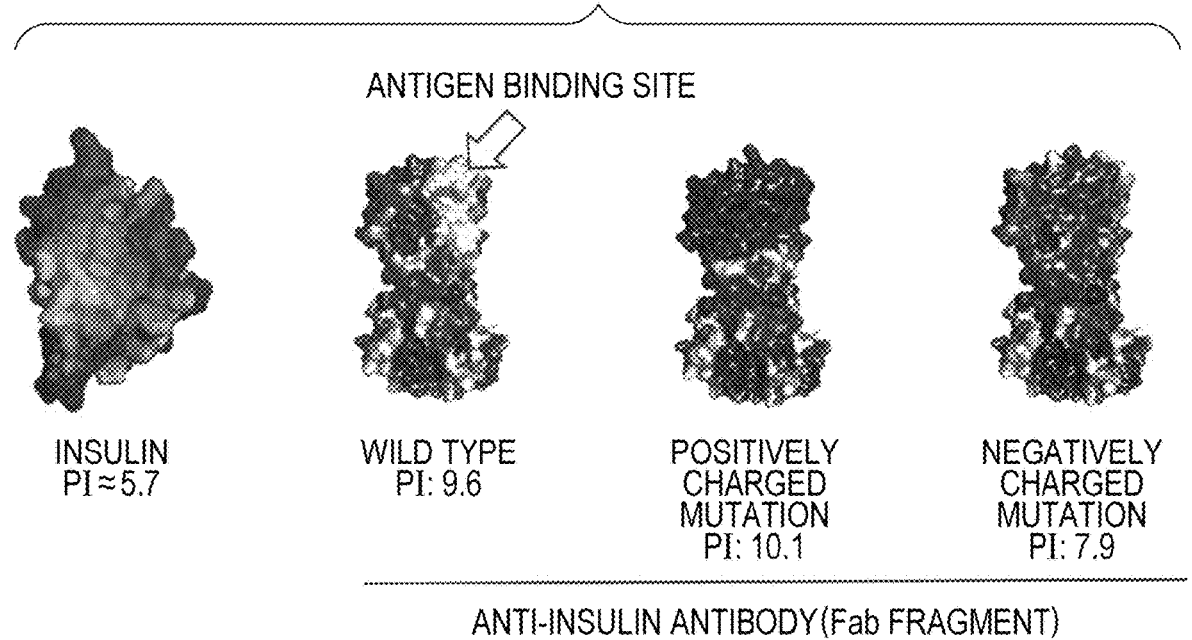
FIG. 2A is a diagram showing the surface charge distribution of a wild-type anti-insulin antibody and its variant, and an antigen (insulin)
Figure 2B:
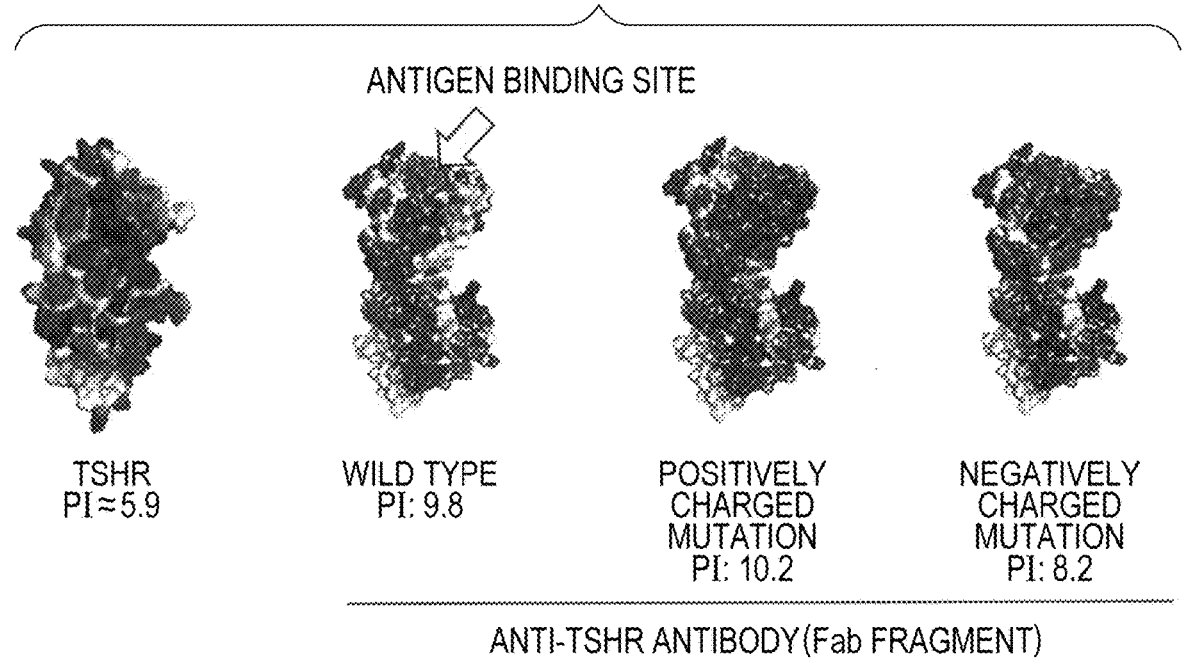
FIG. 2B is a diagram showing the surface charge distribution of a wild-type anti-TSHR antibody and its variant, and an antigen (TSHR)

The surface charge distribution of various Fab fragments prepared in Example 1 was analyzed using a Discovery Studiou (Dassault Systemes BIOVIA). The surface charge distribution diagrams of the Fab fragment of the anti-insulin antibody and insulin as an antigen are shown in FIG. 2A. The surface charge distribution diagrams of the Fab fragment of the anti-TSHR antibody and TSHR as an antigen are shown in FIG. 2B. In the figure, the arrow indicates the antigen-binding site, and PI indicates the value of the isoelectric point. Here, the antigen-binding site is the same as CDR. In the figure, the surface charge distribution is shown in color, indicating that the blue portion is positively charged, the red portion is negatively charged, and the white portion is electrically neutral.

From FIG. 2A, it was found that, in the wild-type anti-insulin antibody, the surface charge of the antigen-binding site is neutral. In the variant type in which a basic amino acid residue was introduced (positively charged mutation) in FR3, a wide range of surface charges including the antigen-binding site was positive. Here, insulin as an antigen is a negatively charged protein, and from FIG. 1A, the affinity for a variant-type antigen in which a positively charged mutation was introduced was improved. On the other hand, in the variant type in which an acidic amino acid was introduced (negatively charged variation) in FR3, a wide range of surface charges including the antigen-binding site was negative. From FIG. 1A, the affinity for the variant-type antigen in which the negatively charged mutation was introduced was reduced. From these facts, it is understood that, in the wild-type anti-insulin antibody, the contribution to the surface charge by charged amino acid residues introduced in FR3 spreads over a wide range.

From FIG. 2B, it was found that, in the wild-type anti-TSHR antibody, the surface charge of the antigen-binding site is negative. In the variant type in which a basic amino acid was introduced (positively charged variation) in FR3, the surface charge in the range excluding the antigen-binding site was positive, but the surface charge of the antigen-binding site did not change much. Here, TSHR as an antigen is a negatively charged protein, but from FIG. 1B, there was no change in affinity for a variant-type antigen in which a positively charged mutation was introduced. On the other hand, in the variant type in which an acidic amino acid was introduced (negatively charged variation) in FR3, a wide range of surface charges including the antigen-binding site was negative. From FIG. 1B, the affinity for the variant-type antigen in which the negatively charged mutation was introduced was reduced. From these facts, it is understood that, in the wild-type anti-TSHR antibody, the contribution to the surface charge by acidic amino acid residues introduced in FR3 spreads over a wide range. On the other hand, even when a basic amino acid residue is introduced in FR3 of the wild-type anti-TSHR antibody, it is understood that the surface charge is locally different.

(2) Relationship Between Electrical Characteristic of Amino Acid Sequence of CDR and Control of Affinity The present inventors considered that the electrical characteristic of CDR of the antibody is related to how the affinity for an antigen changes by introduction of charged amino acid residues in FR3 of the antibody. Here, the present inventors defined the electrical characteristic of CDR by the following formula (I).

$$X = [\text{Number of basic amino acid residues in amino acid sequence of CDR}] - [\text{Number of acidic amino acid residues in amino acid sequence of CDR}] \quad (I)$$

wherein when X is −1, 0 or 1, the electrical characteristic of CDR is neutral, when X is 2 or more, the electrical characteristic of CDR is positively charged, and when X is −2 or less, the electrical characteristic of CDR is negatively charged.

Table 5 shows the amino acid sequence of the light chain CDR of the wild-type anti-TSHR antibody (SEQ ID NOs: 16 and 17). The amino acid sequences of these CDRs are sequences defined by the Chothia method.

TABLE 5

| Antibody | CDR1 | CDR2 | CDR3 | Electrical characteristic of CDR |
|---|---|---|---|---|
| Anti-TSHR antibody | GNSSNIGNNA | YDD | WDDSLDSQ | Negatively charged |

The CDR of the anti-insulin antibody has one basic amino acid residue (arginine), and no acidic amino acid residue exists, thus the electrical characteristic of CDR is defined as neutral (X=1). As shown in Table 5, the CDR of the anti-TSHR antibody has five acidic amino acid residues (aspartic acid), and no basic amino acid residue exists, thus the electrical characteristic of CDR is defined as negatively charged (X=−5). As can be seen from FIGS. 2A and 2B, the electrical characteristics of the CDRs of the anti-insulin antibody and the anti-TSHR antibody determined by the formula (I) are consistent with the surface charge of the antigen-binding site analyzed by Discovery Studiou. Thus, it was found that there are biases in the electrical characteristic of CDR and the surface charge of the antigen-binding site, depending on the antibody.

(3) Results

From the analysis of Example 2 and Example 3, it is suggested that, in the antibody whose electrical characteristic of CDR is neutral, a contribution of the introduction of charged amino acid residue in FR3 is large. It is suggested that, in the antibody whose electrical characteristic of CDR is neutral, it is possible to control the orientation of the antigen-binding site by electrostatic interaction caused by the introduction. On the other hand, it is suggested that, in the antibody whose electrical characteristic of CDR is negatively charged, the effect of electrostatic interaction is topical, even when a basic amino acid residue is introduced in FR3. However, it is suggested that, in the antibody whose electrical characteristic of CDR is negatively charged, it is possible to reduce affinity for an antigen by electrostatic repulsive force when introducing an acidic amino acid residue in FR3.

Example 4

Study on Thermal Stability of Antibody into Which Charged Amino Acid Residue Introduced in FR3

How the thermal stability of each variant of the anti-insulin antibody prepared in Example 1 changes as compared to that of the wild type was examined.

(1) Substitution of Buffer by Gel Filtration

The solvent of the Fab fragment-containing solution obtained in Example 2 was substituted with a buffer (phosphate buffered saline: PBS) used for measurement with a differential scanning calorimeter (DSC) by gel filtration. The conditions of gel filtration are as follows.

[Conditions of Gel Filtration]
Buffer: PBS
Column used: Superdex 200 Increase 10/300 (GE Healthcare)
Column volume (CV): 24 mL
Sample volume: 500 µL
Flow rate: 1.0 mL/min
Elution amount: 1.5 CV
Fraction volume: 500 µL (2) Measurement of Denaturation Temperature (Tm)

Fractions containing Fab fragments were diluted with PBS to prepare Fab fragment-containing samples (final concentration 5 µM). Tm of each Fab fragment was measured using MicroCal VP-Capillary DSC (Malvern Instruments Ltd). The measurement conditions are as follows.

Figure 3:
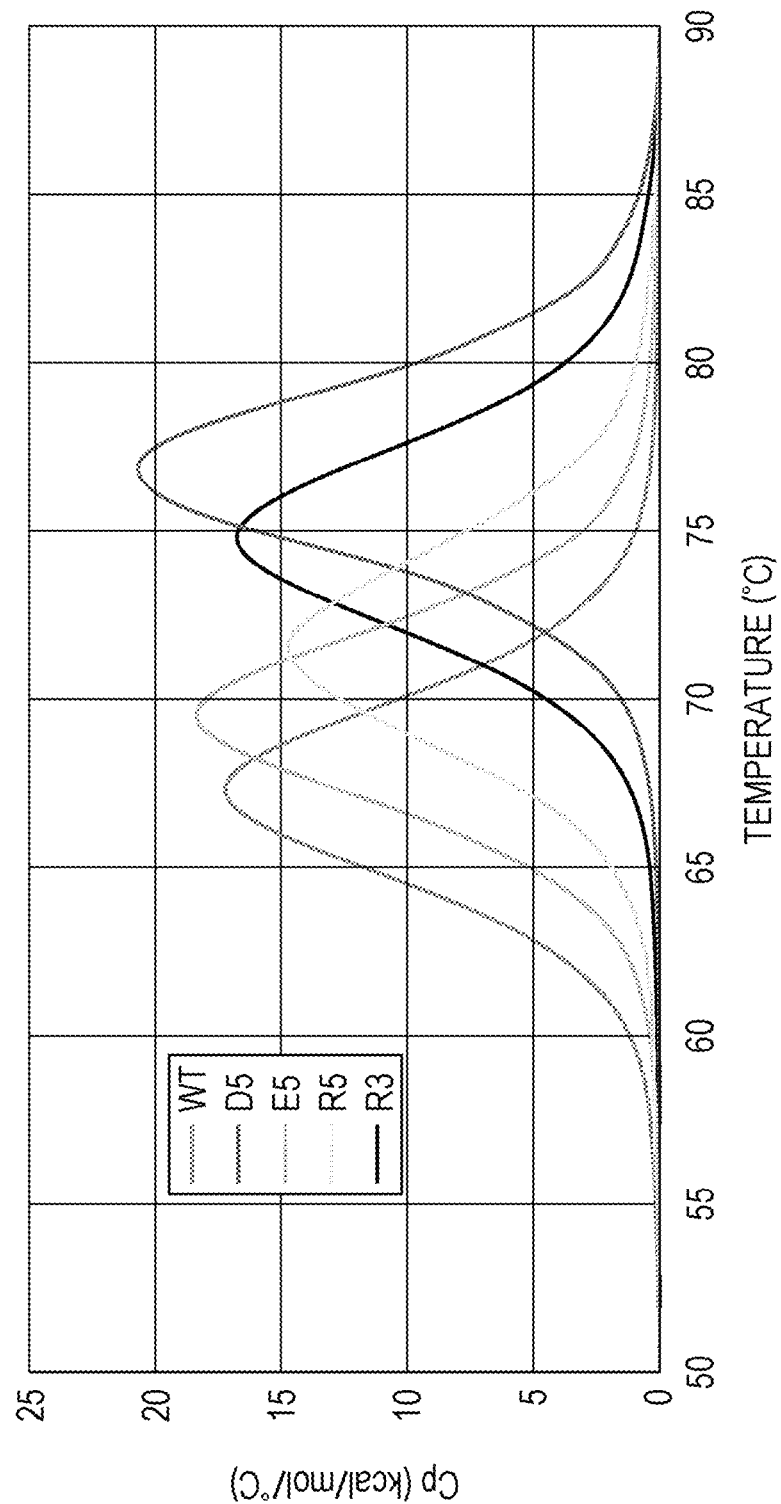
FIG. 3 is a graph showing analytical peaks when the thermal stability of a wild-type anti-insulin antibody and its variant is measured by a differential scanning calorimeter (DSC)

[DSC Measurement Conditions]
Sample amount: 400 µL
Measurement range: 30° C. to 90° C.
Heating rate: 60° C./hour (3) Results The Tm value and analytical peak obtained by DSC measurement are shown in Table 6 and FIG. 3, respectively.

TABLE 6

| Sample | Tm (° C.) |
|---|---|
| Wild type | 76.8 ± 0.087 |
| D5 Variant | 66.9 ± 0.046 |
| E5 Variant | 69.5 ± 0.071 |

TABLE 6-continued

| Sample | Tm (° C.) |
|---|---|
| R5 Variant | 71.1 ± 0.150 |
| R3 Variant | 74.4 ± 0.069 |

The D5 variant showed the lowest thermal stability as compared to the wild type, but the reduction remained only around 13%. In most variants, the thermal stability was found to be almost unchanged from that of the wild type. Thus, it is suggested that the introduction of charged amino acid residue in FR3 hardly affects on the thermal stability of the antibody.

Example 5

Control of Affinity of Anti-Lysozyme Antibody for Antigen

A mutation was introduced in FR3 of an anti-lysozyme antibody based on the electrical characteristic of CDR, and the affinity of the obtained variant for lysozyme was confirmed.

(1) Electrical Characteristic of CDR of Anti-Lysozyme Antibody

Synthesis of anti-lysozyme antibody gene was entrusted to GenScript Japan Inc. to obtain a plasmid DNA containing wild-type anti-lysozyme antibody gene. Based on the base sequence of the gene, the amino acid sequence of the anti-lysozyme antibody was determined. Table 7 shows the amino acid sequences of the light chain CDR and heavy chain CDR of the wild-type anti-lysozyme antibody (SEQ ID NOs: 18 to 23). The amino acid sequences of these CDRs are sequences defined by the Chothia method.

TABLE 7

| | CDR1 | CDR2 | CDR3 |
|---|---|---|---|
| Light chain | RASQSIGNNLH | YASQSIS | QQSNSWPYT |
| Heavy chain | SDYWS | YVSYSGSTYYNPSLKS | WDGDY |

As shown in Table 7, the light chain CDR and heavy chain CDR of the anti-lysozyme antibody have two basic amino acid residues and three acidic amino acid residues. Therefore, the electrical characteristic of CDR of the anti-lysozyme antibody are defined as neutral (X=−1).

(2) Preparation of Variant of Anti-Lysozyme Antibody

Synthesis of genes of R5 variant and D5 variant of anti-lysozyme antibody was entrusted to GenScript Japan Inc. to obtain a plasmid DNA containing variant genes of anti-lysozyme antibody. Here, the R5 variant of the anti-lysozyme antibody is an antibody in which the 63rd, 65th and 67th serine residues, the 70th aspartic acid residue and the 72nd threonine residue of the light chain FR3 defined by the Chothia method in the wild-type antibody are substituted with arginine residues. The D5 variant of the anti-lysozyme antibody is an antibody in which the 63rd, 65th and 67th serine residues, the 70th aspartic acid residue and the 72nd threonine residue of the light chain FR3 defined by the Chothia method in the wild-type antibody are substituted with aspartic acid residues.

Using the obtained plasmid, each antibody was expressed in Expi293 (trademark) cells, and the resulting culture supernatant was purified in the same manner as in Example 1 to obtain each solution of wild-type, R5 variant and D5 variant of anti-lysozyme antibodies.

(3) Measurement of Affinity of Variant for Antigen

A solution (200 ng/mL) prepared by dissolving hen egg white-derived lysozyme (Sigma-Aldrich) in a 10 mM sodium acetate solution (pH 5.0) was used as an antigen of the anti-lysozyme antibody. The antigen was immobilized on the sensor chip for Biacore (registered trademark) Series S Sensor Chip CM5 (GE Healthcare) (41 RU or 33 RU). Solutions of various concentrations were prepared by diluting each antibody solution with HBS EP+buffer (GE Healthcare). These solutions were sent to Biacore (registered trademark) T200 (GE Healthcare). The antibody concentrations and measurement conditions in each solution are as follows. Measurement data was analyzed using Biacore (registered trademark) Evaluation software, and the data on the affinity of each antibody was obtained.

[Antibody Concentrations]
  Wild type: 30 nM, 15 nM, 7.5 nM, 3.75 nM and 1.875 nM
  D5 variant: 30 nM, 15 nM, 7.5 nM, 3.75 nM and 1.875 nM
  R5 variant: 2 nM, 1 nM, 0.5 nM, 0.25 nM and 0.125 nM

[Measurement Conditions]
  Association: 30 µL/min, 60 sec, 120 sec
  Dissociation: 30 µL/min, 60 sec, 1200 sec
  Regeneration: Gly-HCl (pH 2.0)/60 µL/min, 40 sec (4) Results The dissociation constant ($K_D$) was calculated from the binding rate constant ($k_{on}$) and the dissociation rate constant ($k_{off}$) obtained for the wild-type and variants of anti-lysozyme antibodies. The kinetic parameters of each antibody are shown in Table 8 and FIG. 4. In the figure, "negatively charged" indicates the $K_D$ value of the D5 variant, and "positively charged" indicates the $K_D$ value of the R5 variant.

TABLE 8

| Sample | $K_D$ (M) | $K_{on}$ (M$^{-1}$s$^{-1}$) | $K_{off}$ (s$^{-1}$) |
| --- | --- | --- | --- |
| Wild type | $2.34 \times 10^{-10}$ | $4.88 \times 10^5$ | $1.14 \times 10^{-4}$ |
| D5 Variant (negatively charged) | $4.50 \times 10^{-10}$ | $6.07 \times 10^5$ | $2.73 \times 10^{-4}$ |
| R5 Variant (positively charged) | $2.81 \times 10^{-12}$ | $3.34 \times 10^7$ | $9.40 \times 10^{-5}$ |

Figure 4:
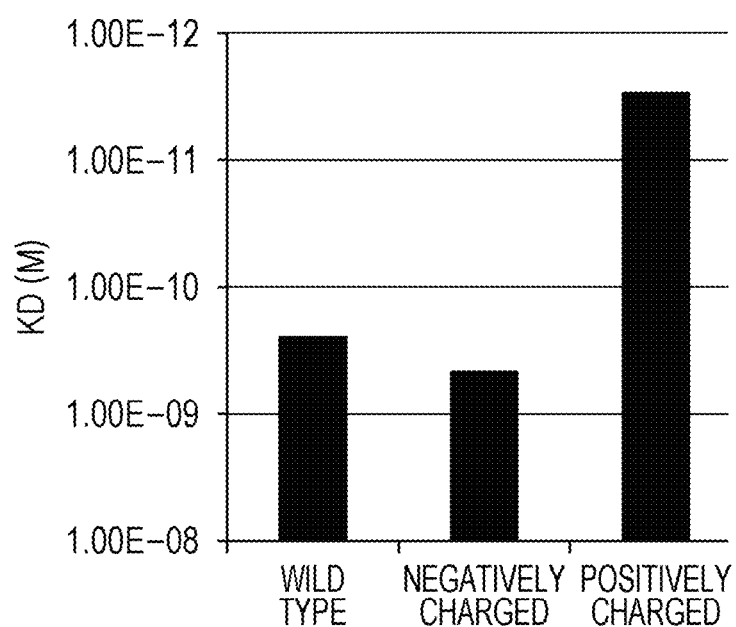
FIG. 4 is a graph showing a dissociation constant in an interaction between a wild-type anti-lysozyme antibody and its variant, and an antigen (lysozyme)

From Table 8 and FIG. 4, the $K_D$ value of the R5 variant of the anti-lysozyme antibody was lower than the $K_D$ value of the wild type. The $K_D$ value of the D5 variant was higher than the $K_D$ value of the wild type. Therefore, as to the anti-lysozyme antibody, it was found that an antibody with affinity for an antigen improved as compared to the wild type can be prepared by mutating 5 neutral amino acid residues of FR3 to basic amino acid residues. It was found that an antibody with affinity for an antigen reduced as compared to the wild type can be prepared by mutating 5 neutral amino acid residues of FR3 to acidic amino acid residues. These results were similar to those of the variant of the anti-insulin antibody in Example 2. Therefore, it is suggested that, in the antibody whose electrical characteristic of CDR is neutral, it is possible to control the orientation of the antigen-binding site by electrostatic interaction caused by the introduction of a charged amino acid residue in FR3.

Example 6

Control of Affinity of Anti-HBsAg Antibody for Antigen

A mutation was introduced in FR3 of an anti-HBsAg antibody based on the electrical characteristic of CDR, and the affinity of the obtained variant for lysozyme was confirmed.

(1) Electrical Characteristic of CDR of Anti-HBsAg Antibody

Hybridomas that produce a mouse anti-HBsAg antibody were prepared by using recombinant HBsAg as an antigen, according to the method described in Kohler and Milstein, Nature, vol. 256, p. 495-497, 1975. A plasmid DNA containing the wild-type anti-HBsAg antibody gene was obtained from RNA of the hybridoma in the same manner as in Example 1. Based on the base sequence of the gene, the amino acid sequence of the anti-HBsAg antibody was determined. It was found that the light chain CDR and heavy chain CDR defined by the Chothia method in the wild-type anti-HBsAg antibody had two basic amino acid residues and ten acidic amino acid residues. Therefore, the electrical characteristic of CDR of the anti-HBsAg antibody are defined as negatively charged (X=−8).

(2) Preparation of Variant of Anti-HBsAg Antibody

In order to introduce a mutation in the light chain FR3 defined by the Chothia method, PCR was carried out in the same manner as in Example 1, using the wild-type anti-HBsAg antibody gene obtained in the above (1) and the primer represented by the following base sequence.

[Primer of Anti-HBsAg Antibody]

```
D5 variant FOR:
                                    (SEQ ID NO: 24)
5' GGGACCGATTATGATCTCACAATCAGTCGAATGGAG 3'

D5 variant REV:
                                    (SEQ ID NO: 25)
5' ATCCCCATCGGCATCGAAACGAACAGGGACTCCAGAAGC 3'
```

Using the obtained PCR product, a plasmid containing a gene encoding a variant or wild-type light chain and a plasmid containing a gene encoding a wild-type heavy chain were obtained in the same manner as in Example 1. Using these plasmids, each antibody was expressed in Expi293 (trademark) cells, and the resulting culture supernatant was purified in the same manner as in Example 1 to obtain each solution of wild-type and D5 variant of anti-HBsAg antibodies. Here, the D5 variant of the anti-HBsAg antibody is an antibody in which the 63rd, 65th, 67th and 70th serine residues and the 72nd phenylalanine residue of the light chain FR3 defined by the Chothia method in the wild-type antibody are substituted with aspartic acid residues.

(3) Measurement of Affinity of Variant for Antigen (3.2) Immobilization of Capture Antibody The capture antibody was immobilized on each well of a plate (NUNC-immuno module, Cat No. 469949, manufactured by NUNC Co., Ltd.) in the same manner as in Example 2, except for using a mouse anti-HBsAg antibody produced from a hybridoma different from the hybridoma obtained in the above (1) as a capture antibody. Each well of the plate was blocked with a blocking solution (PBS containing 1% BSA) in the same manner as in Example 2.

(3.3) Primary Reaction

As the antigen of the anti-HBsAg antibody, HISCL (registered trademark) HBsAg calibrator (HBsAg concentration 0.025 IU/mL, Sysmex Corporation) was used. The blocking solution was removed from the plate on which the capture antibody was immobilized, and 50 µL each of the antigen solution was added to each well. This plate was shaken at room temperature for 60 minutes to perform an antigen-antibody reaction.

(3.3) Secondary Reaction and Detection

The wild-type and D5 variant of anti-HBsAg antibodies were used as detection antibodies. Each antibody was stepwise diluted with PBS containing 1% BSA to obtain antibody solutions at concentrations of 400 nM, 80 nM, 16 nM, 3.2 nM, 640 pM, 128 pM, 25.6 pM and 5.12 pM. HRP-labeled anti-mouse IgG (Fc specific) antibody was used as a secondary antibody. Using these, an antigen-antibody reaction was performed in the same manner as in Example 2. Then, the absorbance at 450 nm was measured for each well of the plate using 1-Step Ultra TMB-ELISA Substrate Solution (Thermo Fisher Scientific) as a substrate solution in the same manner as in Example 2.

(4) Results

The dissociation constant ($K_D$) was calculated from the measurement value of the ELISA method using the wild-type and D5 variant of anti-HBsAg antibodies. The results are shown in Table 9 and FIG. 5. In the figure, "negatively charged" indicates the $K_D$ value of the D5 variant.

TABLE 9

| Sample | $K_D$ (M) |
|---|---|
| Wild type | $2.00 \times 10^{-10}$ |
| D5 Variant (negatively charged) | $3.00 \times 10^{-9}$ |

Figure 5:
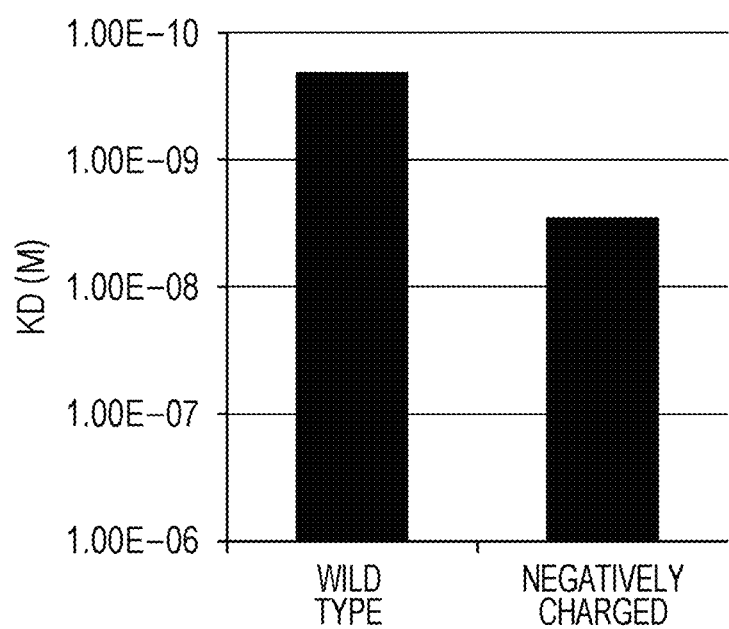
FIG. 5 is a graph showing a dissociation constant in an interaction between a wild-type anti-hepatitis B surface antigen (HBsAg) antibody and its variant, and an antigen (HBsAg).

From Table 9 and FIG. 5, the $K_D$ value of the D5 variant of the anti-HBsAg antibody was higher than the $K_D$ value of the wild type. The $K_D$ value of the D5 variant was higher than the $K_D$ value of the wild type. Therefore, as to the anti-HBsAg antibody, it was found that an antibody with affinity for an antigen reduced as compared to the wild type can be prepared by mutating 5 neutral amino acid residues of FR3 to acidic amino acid residues. These results were similar to those of the D5 variant and the E5 variant of the anti-TSHR antibodies in Example 2. Therefore, it is suggested that, in the antibody whose electrical characteristic of CDR is negatively charged, it is possible to reduce affinity for an antigen by electrostatic repulsive force generated by the introduction of an acidic amino acid residue in FR3.

What is claimed is:

1. A method for increasing affinity of an antibody for an antigen, said method comprising substituting, in a light chain of an antibody that has an electrical characteristic value (X) of −1, 0 or 1, at least 3 amino acid residues selected from the group consisting of positions 63, 65, 67, 70 and 72 as defined by the Chothia method each independently with an arginine residue or a lysine residue, to thereby increase the affinity of the antibody for said antigen, wherein X is calculated by the following formula:

$X$=[total number of basic amino acid residues in all complementarity-determining regions (CDRs) in the antibody]−[total number of acidic amino acid residues in all CDRs in the antibody], wherein the CDRs are defined by the Chothia method.

2. The method according to claim 1, wherein the antibody is in the form of an antibody fragment.

3. The method according to claim 2, wherein the antibody fragment is a Fab fragment.

4. A method for producing an antibody with increased affinity for an antigen, wherein said method comprises the steps of:

substituting, in a light chain of an antibody that has an electrical characteristic value (X) of −1, 0 or 1, at least 3 amino acid residues selected from the group consisting of positions 63, 65, 67, 70 and 72 as defined by the Chothia method each independently with an arginine residue or a lysine residue, to thereby increase the affinity of the antibody for said antigen; and recovering the antibody obtained in the substitution step, wherein X is calculated by the following formula:

$X$=[total number of basic amino acid residues in all complementarity-determining regions (CDRs) in the antibody]−[total number of acidic amino acid residues in all CDRs in the antibody], wherein the CDRs are defined by the Chothia method.

* * * * *

SEQUENCE LISTING

```
<160> NUMBER OF SEQ ID NOS: 25

<210> SEQ ID NO 1
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 1
ttcgtattcg gtcccttccc cttcgccttc aaagcgagca                            40

<210> SEQ ID NO 2
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 2
atcgtaatcg gtcccatccc catcgccatc aaagcgagca                            40

<210> SEQ ID NO 3
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 3
cttgtacttg gtccccttcc ccttgccctt aaagcgagca                            40

<210> SEQ ID NO 4
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 4
tctgtatctg gtccctctcc ctctgcctct aaagcgagca                            40

<210> SEQ ID NO 5
<211> LENGTH: 18
```

```
<212> TYPE: DNA
<213> ORGANISM: Artificial Sequence
<220> FEATURE:
<223> OTHER INFORMATION: Synthetic oligonucleotide primer

<400> SEQUENCE: 5
ctcacaatca gctgattg                                                   18

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 6
tctccctctg cctctaaagc gagca                                           25

<210> SEQ ID NO 7
<211> LENGTH: 15
<212> TYPE: DNA
<213> ORGANISM: Artificial Sequence
<220> FEATURE:
<223> OTHER INFORMATION: Synthetic oligonucleotide primer

<400> SEQUENCE: 7
gggaccagat acaga                                                      15

<210> SEQ ID NO 8
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 8
ggcacagacg ccgacctggc aatca                                           25

<210> SEQ ID NO 9
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 9
gtcccggtct ccgtcaaacc ggtcg                                           25

<210> SEQ ID NO 10
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 10
ggcacagagg ccgagctggc aatca                                           25

<210> SEQ ID NO 11
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 11
```
ctcccgctct ccctcaaacc ggtcg                                                25

<210> SEQ ID NO 12
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 12
ggcacaaagg ccaagctggc aatca                                                25

<210> SEQ ID NO 13
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 13
cttccgcttt cccttaaacc ggtcg                                                25

<210> SEQ ID NO 14
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 14
ggcacaaggg ccaggctggc aatca                                                25

<210> SEQ ID NO 15
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 15
cctccgcctt cccctaaacc ggtcg                                                25

<210> SEQ ID NO 16
<211> LENGTH: 10
<212> TYPE: PRT
<213> ORGANISM: Homo sapiens

<400> SEQUENCE: 16

Gly Asn Ser Ser Asn Ile Gly Asn Asn Ala
1               5                   10

<210> SEQ ID NO 17
<211> LENGTH: 8
<212> TYPE: PRT
<213> ORGANISM: Homo sapiens

<400> SEQUENCE: 17

Trp Asp Asp Ser Leu Asp Ser Gln
1               5

<210> SEQ ID NO 18
<211> LENGTH: 11
<212> TYPE: PRT
<213> ORGANISM: Mus musculus

<400> SEQUENCE: 18

Arg Ala Ser Gln Ser Ile Gly Asn Asn Leu His
1               5                   10

<210> SEQ ID NO 19
<211> LENGTH: 7
<212> TYPE: PRT
<213> ORGANISM: Mus musculus

<400> SEQUENCE: 19

Tyr Ala Ser Gln Ser Ile Ser
1               5

<210> SEQ ID NO 20
<211> LENGTH: 9
<212> TYPE: PRT
<213> ORGANISM: Mus musculus

<400> SEQUENCE: 20

Gln Gln Ser Asn Ser Trp Pro Tyr Thr
1               5

<210> SEQ ID NO 21
<211> LENGTH: 5
<212> TYPE: PRT
<213> ORGANISM: Mus musculus

<400> SEQUENCE: 21

Ser Asp Tyr Trp Ser
1               5

<210> SEQ ID NO 22
<211> LENGTH: 16
<212> TYPE: PRT
<213> ORGANISM: Mus musculus

<400> SEQUENCE: 22

Tyr Val Ser Tyr Ser Gly Ser Thr Tyr Tyr Asn Pro Ser Leu Lys Ser
1               5                   10                  15

<210> SEQ ID NO 23
<211> LENGTH: 5
<212> TYPE: PRT
<213> ORGANISM: Mus musculus

<400> SEQUENCE: 23

Trp Asp Gly Asp Tyr
1               5

<210> SEQ ID NO 24
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 24
gggaccgatt atgatctcac aatcagtcga atggag                          36

<210> SEQ ID NO 25
<211> LENGTH: 39
<212> TYPE: DNA
<213> ORGANISM: Artificial Sequence
<220> FEATURE:
<223> OTHER INFORMATION: Synthetic oligonucleotide primer

```
<400> SEQUENCE: 25
atccccatcg gcatcgaaac gaacagggac tccagaagc                              39
```